United States Patent [19]
Ohmori et al.

[11] Patent Number: 5,619,792
[45] Date of Patent: Apr. 15, 1997

[54] METHOD AND DEVICE FOR ILLUMINATION IN TERMINATED CABLE PART INSPECTION DEVICE FOR STRIPPED TERMINAL CRIMPING MACHINE

[75] Inventors: Hideki Ohmori; Yoshihide Ichikawa, both of Yokkaichi, Japan

[73] Assignee: Sumitomo Wiring Systems, Ltd., Japan

[21] Appl. No.: 572,419

[22] Filed: Dec. 14, 1995

[30] Foreign Application Priority Data

Dec. 22, 1994 [JP] Japan .................................. 6-320789

[51] Int. Cl.$^6$ ..................... H01R 43/048; F21V 33/00; F21V 21/14
[52] U.S. Cl. ................. 29/863; 29/721; 29/753; 29/759; 362/33; 362/271; 362/285
[58] Field of Search ................. 29/720, 721, 753, 29/748, 759, 833, 863, 712; 72/712; 362/32, 33, 253, 271, 285

[56] References Cited

U.S. PATENT DOCUMENTS

| | | | |
|---|---|---|---|
| 2,805,471 | 10/1957 | Lowden | 29/721 X |
| 3,913,202 | 10/1975 | Pyle et al. | 29/721 |
| 4,973,216 | 11/1990 | Domm | 29/759 X |
| 5,212,880 | 5/1993 | Nishiguchi et al. | 29/833 X |
| 5,249,349 | 10/1993 | Kuinose et al. | 29/721 |
| 5,521,800 | 5/1996 | Pine et al. | 362/285 X |

FOREIGN PATENT DOCUMENTS 55386  3/1994  Japan ........................ 29/721

OTHER PUBLICATIONS

Copy of Japanese Patent Application No. 61-133844 entitled Pressure-Connected Parts of Terminals of Wires with Pressure-Connected Terminals (8 pages).

*Primary Examiner*—Peter Vo
*Attorney, Agent, or Firm*—Jordan B. Bierman; Bierman and Muserlian

[57] ABSTRACT

An illuminating device for use in a terminated cable part inspection device for a stripped terminal crimping machine is of a reflected image capturing type and can ensure a satisfactory illuminance required for photographing. The stripped terminal crimping machine includes a stripping portion and a terminal crimping portion between which the terminated cable part inspection device (8) is located on a bidirectional path (P). The terminated cable part inspection device (8) includes an image pickup camera (11) having a high shutter speed, an illuminating means (12), and a detecting means (13) including first and second sensors (31, 32) for detecting the cable. The illuminating means (12) includes a pair of illuminating portions (20) on opposite sides of a photographing path (19) of the image pickup camera (11) for directing illumination in substantially the same direction as a photographing direction toward a cable end passing therethrough along the bidirectional path (P) and elongated in substantially the same direction as a longitudinal direction of the cable. The illuminating portions (20) are arranged in inwardly inclined relation.

9 Claims, 41 Drawing Sheets

F I G. 10A
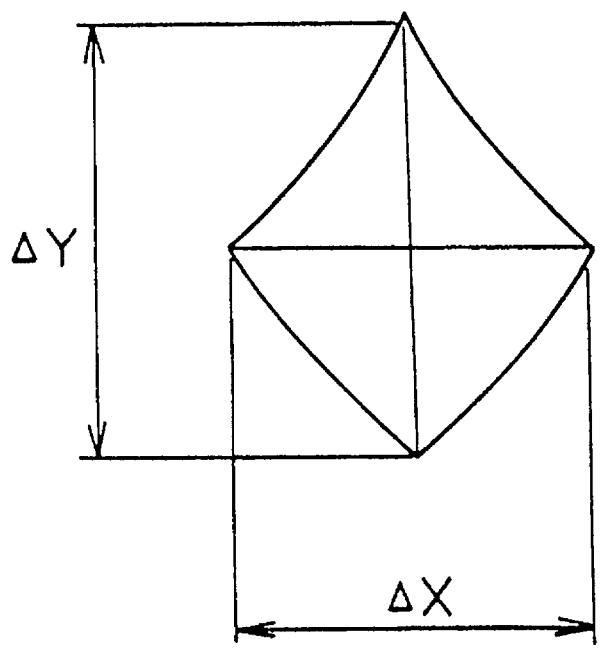
F I G. 10B
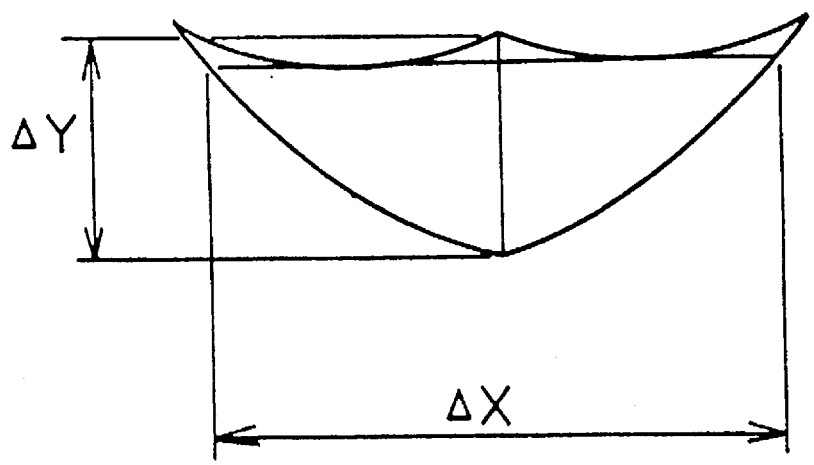

METHOD AND DEVICE FOR ILLUMINATION IN TERMINATED CABLE PART INSPECTION DEVICE FOR STRIPPED TERMINAL CRIMPING MACHINE

BACKGROUND OF THE INVENTION

1. Field of the Invention

The present invention relates to a method and device for illumination in a terminated cable part inspection device for a stripped terminal crimping machine which inspects stripped parts and terminal crimped parts of cables on a bidirectional path along which cable ends are transported.

2. Description of the Background Art

Conventional inspection of the stripping conditions of a coating-removed stripped part at a cable end and the crimping conditions of a terminal crimped part formed by crimping a crimp terminal to the stripped part by means of image processing generally involves photographing the stripped part and terminal crimped part by an image pickup means such as a television camera and two-dimensional CCD camera, displaying the image photographed by the image pickup means on a monitoring television receiver, processing the image by an image processing means, judging whether or not the stripping and crimping conditions are defective, and displaying the result of judgement by means of a printer or display unit.

A device for such inspection includes a keyboard for operation which is used to input program data and the like required for image processing.

This type of inspection device is disclosed in, for example, Japanese Patent Application Laid-Open No. 61-133844(1986). In this disclosure, a stripping portion strips the coating of a cable at a cable end held by a cable holding portion of an arm. The arm is pivoted to transport the stripped part of the cable at the cable end to a terminal crimping portion which in turn crimps a crimp terminal to the stripped part. The arm is then pivoted in the opposite direction to transport the terminal crimped part of the cable to the stripping position. The cable is transported by a predetermined length in a predetermined direction and cut in position. Cables are sequentially subjected to the stripping and terminal crimping by the similar procedure.

The inspection device for inspecting the stripping and crimping conditions is provided on a bidirectional path along which the cable is transported between the stripping portion and terminal crimping portion.

The inspection device comprises a light source and a television camera on opposite sides of the bidirectional path, and a sensor including a light projector and a light receiver on opposite sides thereof for detecting a cable photographing timing. The sensor detects the stripped part and terminal crimped part passing therethrough, and the light source emits light in response to the detection output of the sensor. The television camera photographs the silhouette image of the stripped and terminal crimped parts, and an image processor captures and processes the silhouette image. In this manner, whether or not the stripping and crimping conditions are defective is determined.

However, the inspection device disclosed in Japanese Patent Application Laid-Open No. 61-133844 is of the type wherein the silhouette image is captured, that is, only the outline information of the silhouette is captured. The inspection device receives a small amount of image information and is incapable of detecting crimping failures and cores extending off in the silhouette portion, resulting in inaccurate inspection.

Another inspection device is of the type wherein an object to be inspected is illuminated from the photographing direction of the image pickup means to capture a reflected image for receiving more image information. However, this inspection device is designed to photograph the stationary object to be inspected in a predetermined inspection position. Thus, illumination by a lighting fixture is only required to ensure an illuminance needed for photographing in the predetermined inspection position.

However, in the above stated stripped terminal crimping machine, the cable end held by the arm in cantilevered fashion and typically moved along the bidirectional path at high speeds of about 2000 mm/s is photographed. This causes the distal end of the cable moved in a first direction along the bidirectional path to deflect slightly rearwardly in the transport direction. On the other hand, the cable end moved in a second direction opposite from the first direction along the bidirectional path is weighted with the crimp terminal crimped thereto, causing the distal end of the cable to deflect by a greater amount rearwardly in the opposite transport direction. The attitude of the stripped cable end when photographed is greatly deviated along the bidirectional path from the attitude of the terminal-crimped cable end when photographed. The attitude of the cable end when photographed and the location of the cable end when passing along the bidirectional path are deviated depending on the cable diameter and the crimp terminal types. It is hence necessary to ensure a certain range of illuminance required for photographing.

SUMMARY OF THE INVENTION

A first aspect of the present invention is directed to a method for illumination in a terminated cable part inspection device for a stripped terminal crimping machine, the stripped terminal crimping machine comprising a stripping portion for stripping a coating at an end of a cable, a terminal crimping portion for crimping a crimp terminal to the stripped end of the cable, and a transport mechanism for transporting the stripped cable end in a first direction along a bidirectional path from an initial position of the bidirectional path to the terminal crimping portion and then transporting the stripped cable end in a second direction along the bidirectional path from the terminal crimping portion to the initial position after crimping of the crimp terminal, the terminated cable part inspection device for photographing the cable end transported along the bidirectional path to inspect a stripped part and a terminal crimped part of the cable by image processing, the terminated cable part inspection device including an image pickup camera for photographing the cable end, and illuminating means for illuminating the cable end to be photographed by the image pickup camera, the illuminating means including a pair of illuminating portions on opposite sides of a photographing path of the image pickup camera for directing illumination in substantially the same direction as a photographing direction of the image pickup camera toward the cable end passing therethrough along the bidirectional path, the pair of illuminating portions being elongated in substantially the same direction as a longitudinal direction of the cable. According to the present invention, the method is characterized by directing illumination by the pair of illuminating portions in inwardly angled directions respectively from the opposite sides of the photographing path of the image pickup camera toward the cable end passing therethrough along the bidirectional path.

A second aspect of the present invention is directed to an illuminating device for use in a terminated cable part inspection device for a stripped terminal crimping machine, the stripped terminal crimping machine comprising a stripping portion for stripping a coating at an end of a cable, a terminal crimping portion for crimping a crimp terminal to the stripped end of the cable, and a transport mechanism for transporting the stripped cable end in a first direction along a bidirectional path from an initial position of the bidirectional path to the terminal crimping portion and then transporting the stripped cable end in a second direction along the bidirectional path from the terminal crimping portion to the initial position after crimping of the crimp terminal, the terminated cable part inspection device for photographing the cable end transported along the bidirectional path to inspect a stripped part and a terminal crimped part of the cable by image processing, the terminated cable part inspection device including an image pickup camera for photographing the cable end, and illuminating means for illuminating the cable end to be photographed by the image pickup camera, the illuminating means including a pair of illuminating portions on opposite sides of a photographing path of the image pickup camera for directing illumination in substantially the same direction as a photographing direction of the image pickup camera toward the cable end passing therethrough along the bidirectional path, the pair of illuminating portions being elongated in substantially the same direction as a longitudinal direction of the cable. According to the present invention, the pair of illuminating portions are arranged in inwardly inclined relation.

According to the method and device of the first and second aspects of the present invention, the illuminating portions for directing illumination in substantially the same direction as the photographing direction of the image pickup camera toward the cable end passing therethrough along the bidirectional path are located on opposite sides of the photographing path of the image pickup camera and are elongated in substantially the same direction as the longitudinal direction of the cable to be transported. The illuminating portions direct illumination in inwardly angled directions respectively from the opposite sides of the photographing path of the image pickup camera toward the cable end passing therethrough along the bidirectional path. The interference of illuminated light from the illuminating portions ensures a stable illuminance along the bidirectional path.

Therefore, a sufficient illuminance for photographing the end of the cable moved along the bidirectional path is satisfactorily ensured when differences in photographing attitude and bidirectional path passing position occur between the stripped end of the cable moved in the first direction and the end of the cable with the crimp terminal crimped thereto and moved in the second direction and when the diameter of the cable and the type of the crimp terminal are varied. This allows satisfactory capturing of the reflected image of the moving cable end, thereby providing a great amount of image information and achieving inspection using more correct image information.

It is therefore an object of the present invention to provide a method and device for illumination in a terminated cable part inspection device for a stripped terminal crimping machine which is of a reflected image capturing type and which can ensure a satisfactory illuminance required for photographing.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 10A and 10B illustrate horizontal and vertical lengths of regions;

DESCRIPTION OF THE PREFERRED EMBODIMENTS

Figure 1:
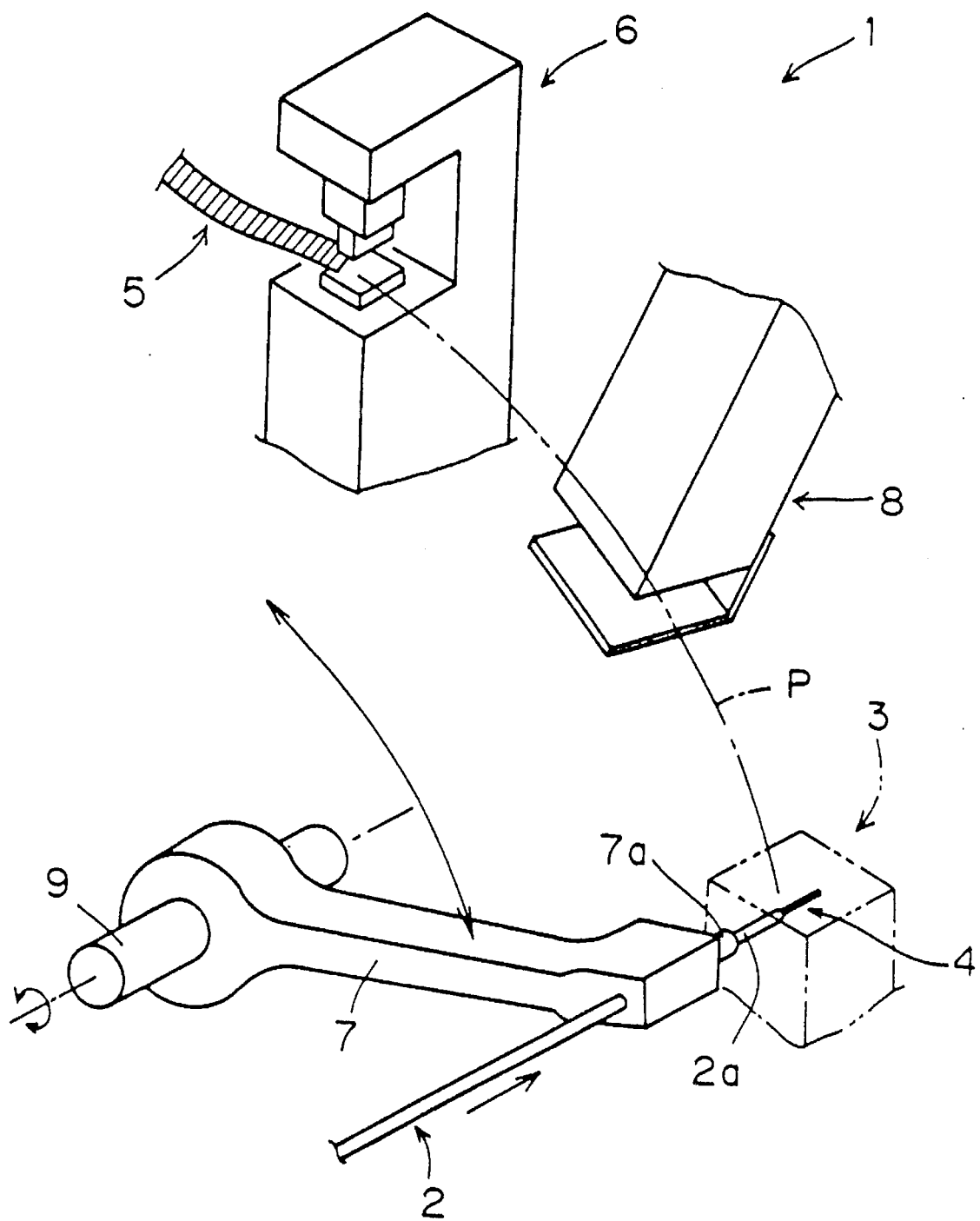
FIG. 1 schematically illustrates essential portions of a stripped terminal crimping machine according to a preferred embodiment of the present invention.

A preferred embodiment according to the present invention will now be described with reference to the drawings. Referring to FIGS. 1 through 8, a stripped terminal crimping machine 1, like the conventional machine, comprises a stripping portion 3 for stripping a coating 2a at an end of each cable 2 sequentially fed; a terminal crimping portion 6 for crimping a crimp terminal 5 to a stripped part 4 of the cable 2 at the stripped end; a transport arm 7 for holding the cable 2 adjacent one end thereof for transporting the end of the cable 2 between the stripping portion 3 and the terminal crimping portion 6 in a reciprocal manner; and a terminated cable part inspection device 8 located on a bidirectional path P of the end of the cable 2.

The stripping portion 3 suitably includes a cutting blade for severing the cable 2 and a stripping blade for cutting through the coating 2a, and is controlled to cut and strip the cable 2.

The terminal crimping portion 6 includes a crimping machine. The terminal crimping portion 6 feeds successive crimp terminals 5 one by one to a crimping position in the crimping machine and is controlled to crimp one crimp terminal 5 to the stripped part 4.

The transport arm 7 includes a cable clamp portion 7a for releasably holding the cable 2. The transport arm 7 is pivoted on a support shaft 9, with the cable 2 held by the cable clamp portion 7a, and is controlled to transport the end of the cable 2 in a reciprocal manner along the bidirectional path P at high speeds (for example, about 2000 mm/s).

The terminated cable part inspection device 8 includes an image pickup camera 11, such as a television camera and two-dimensional CCD camera, serving as an image pickup means for photographing the end of the cable 2 transported along the bidirectional path P; an illuminating means 12 for illuminating the end of the cable 2 transported along the bidirectional path P; and a detecting means 13 for detecting the photographing timing of the end of the cable 2 transported along the bidirectional path P.

The image pickup camera 11 employs a camera having a superfast shutter function such that the shutter speed is fast (for example, 1/30000 sec.), and is angularly adjustably mounted at a predetermined angle to a mounting bracket 14 on the base of the stripped terminal crimping machine 1. The image pickup camera 11 includes a camera body 15, an extension tube 16, and a lens portion 17.

Figure 4:
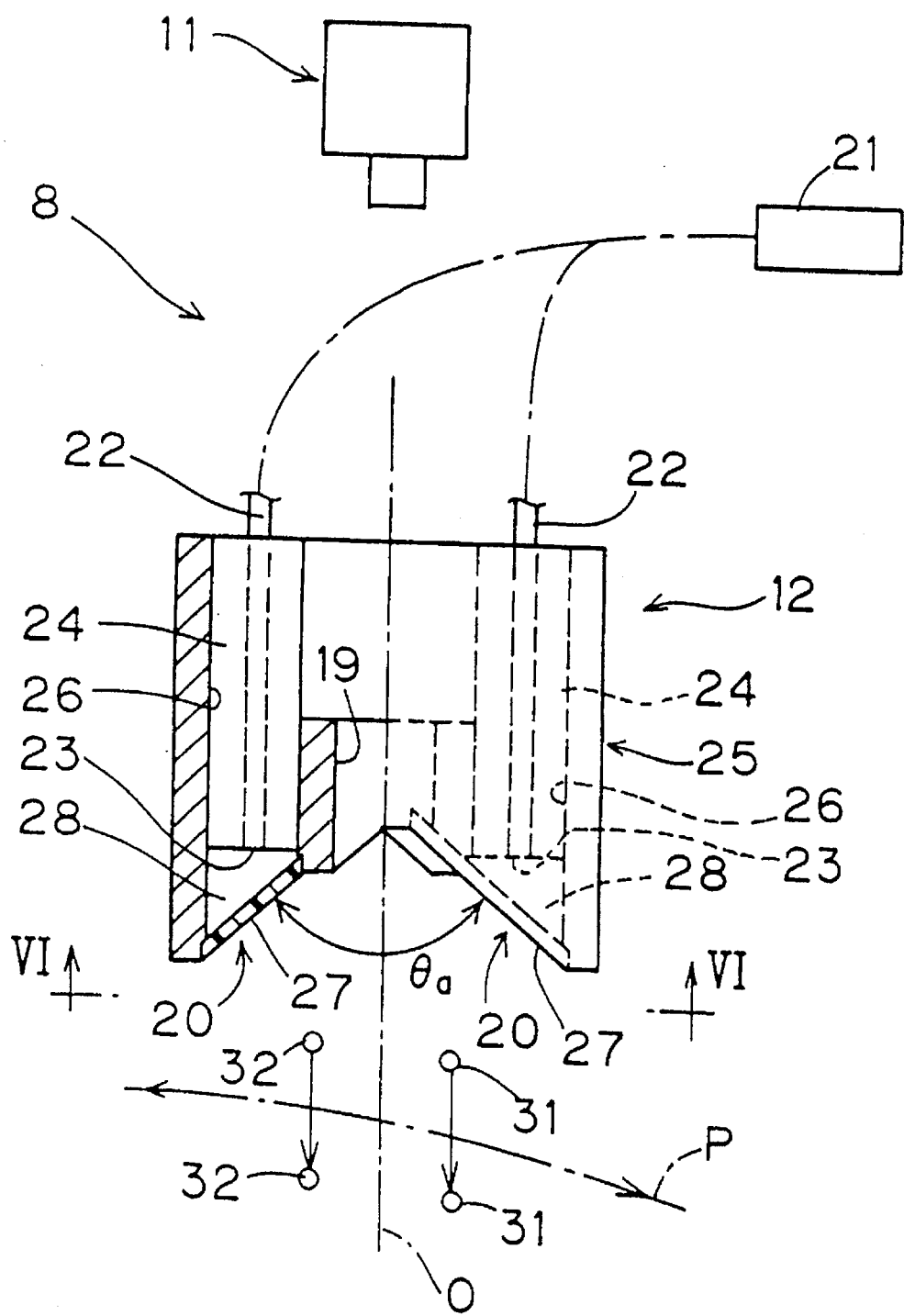
FIG. 4 illustrates an illuminating means.
Figure 5:
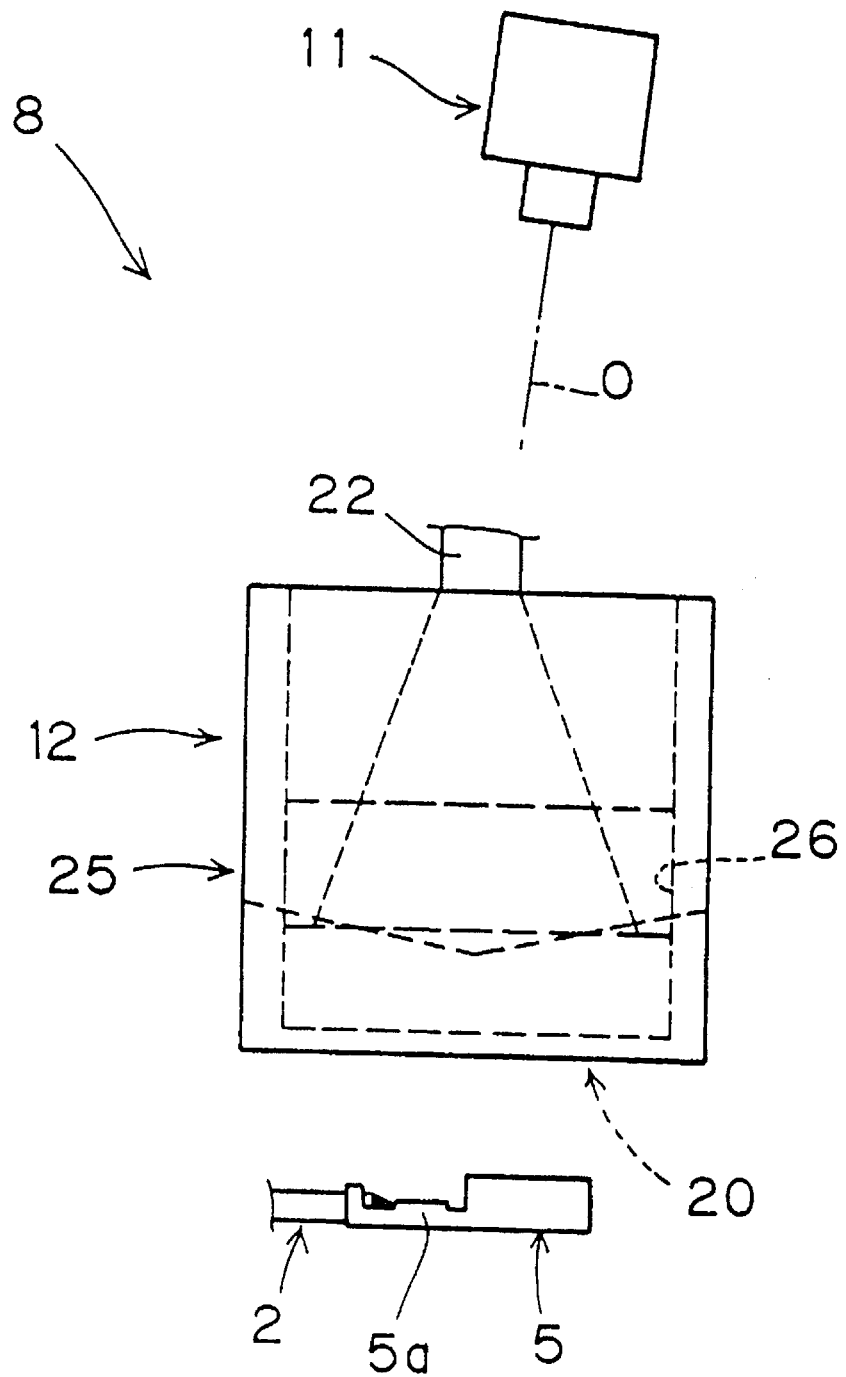
FIG. 5 is a right side view of FIG. 4.
Figure 6:
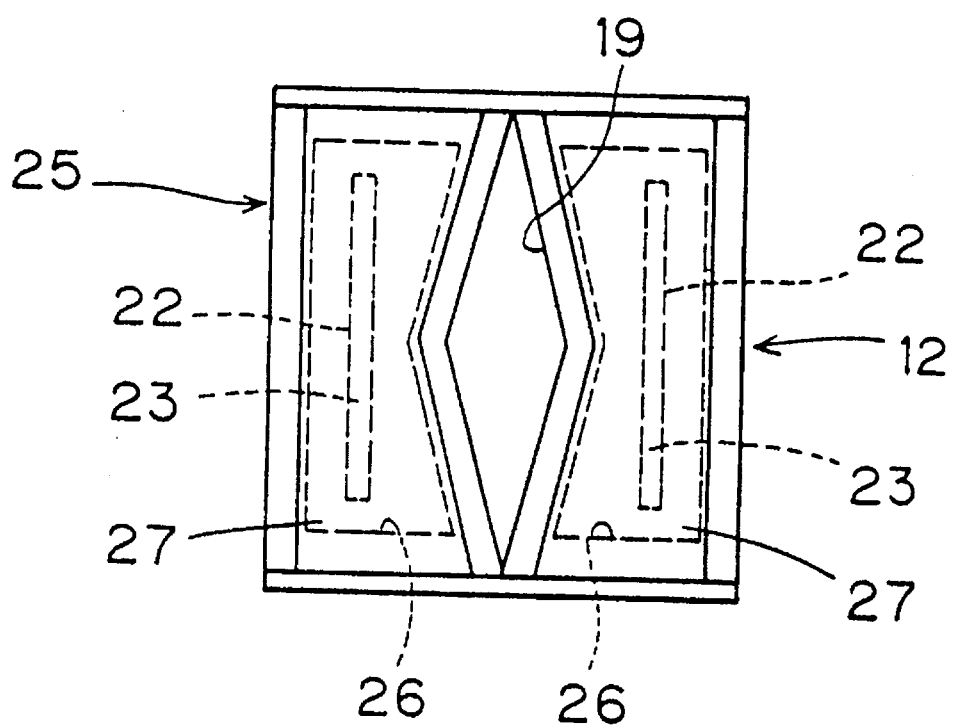
FIG. 6 is a view in the direction of the arrows VI—VI of FIG. 4.

As shown in FIGS. 4 through 6, the illuminating means 12 serves as an illuminating device according to the present invention and includes a pair of illuminating portions 20 located on opposite sides of a photographing path 19 of the image pickup camera 11 for directing illumination in substantially the same direction as the photographing direction of the image pickup camera 11 toward the end of the cable 2 passing therethrough along the bidirectional path P, a lamp housing 21 located in a separate position and includes a light source such as a halogen lamp, and optical fibers 22 made of quartz, plastic and the like for guiding the light emitted from the light source to the pair of illuminating portions 20.

The distal end of each optical fiber 22 adjacent the illuminating portions 20 is of a flat and fan-shaped configuration flared gradually toward the end. Light projecting portions 23 formed in the distal end surfaces of the optical fibers 22 are held by fiber array holders 24 so that they are elongated in substantially the same direction as the longitudinal direction of the cable 2 passing therethrough. The fiber array holders 24 are securely mounted in an illumination holder 25.

The illumination holder 25 is of a hollow, cuboid-shaped configuration. The photographing path 19 defined by a rhombic aperture along an optical axis 0 of the image pickup camera 11 is formed centrally of the illumination holder 25. A pair of illuminating portion mounting apertures 26 are provided on opposite sides of the photographing path 19. The fiber array holders 24 are respectively inserted from above into the illuminating portion mounting apertures 26 and securely mounted in the illumination holder 25 with screws and the like.

A pair of transmitted light scattering plates 27 made of ground glass or acrylic board for closing the respective illuminating portion mounting apertures 26 are securely mounted with screws and the like on the bottom of the illuminating portion mounting apertures 26 suitably spaced apart from the light projecting portions 23 of the optical fibers 22. The pair of transmitted light scattering plates 27 are inwardly inclined to form a suitable angle θa as shown in FIG. 4. Spacings surrounded by the light projecting portions 23 and transmitted light scattering plates 27 are defined as spacings 28 for diffusing the light guided by the optical fibers 22.

The illumination holder 25 is mounted in a predetermined attitude to a mounting bracket 29 on the base of the stripped terminal crimping machine 1.

The detecting means 13 includes a first sensor 31 for detecting the timing of photographing the end of the cable 2 transported in one direction (a first direction) along the bidirectional path P by the image pickup camera 11, and a second sensor 32 for detecting the timing of photographing the end of the cable 2 transported in the opposite direction (a second direction) along the bidirectional path P by the image pickup camera 11. The sensors 31, 32 are mounted to a sensor mounting bracket 33 in a position deviated from the optical axis O of the image pickup camera 11.

Figure 2:
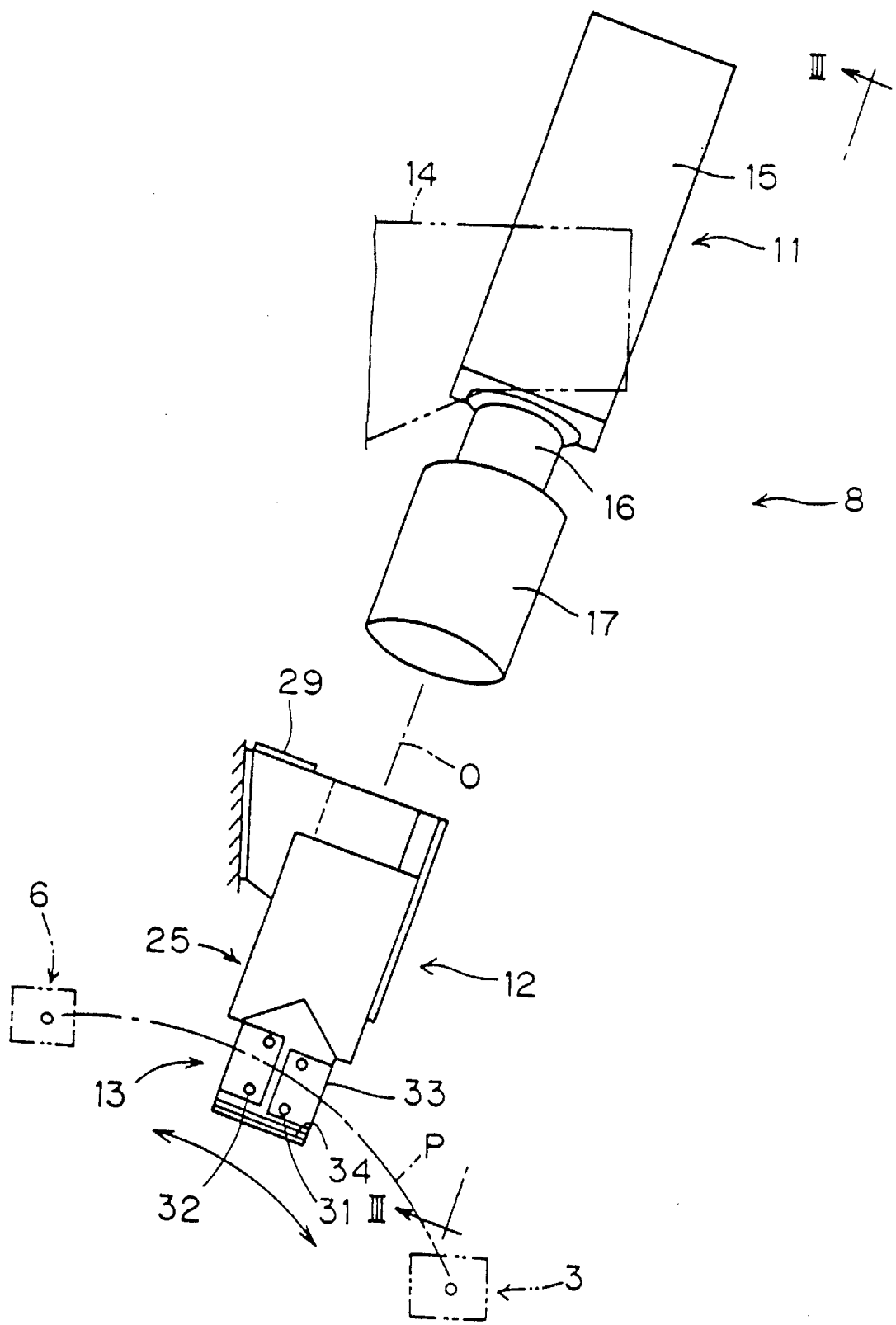
FIG. 2 schematically illustrates a terminated cable part inspection device according to the preferred embodiment of the present invention.
Figure 3:
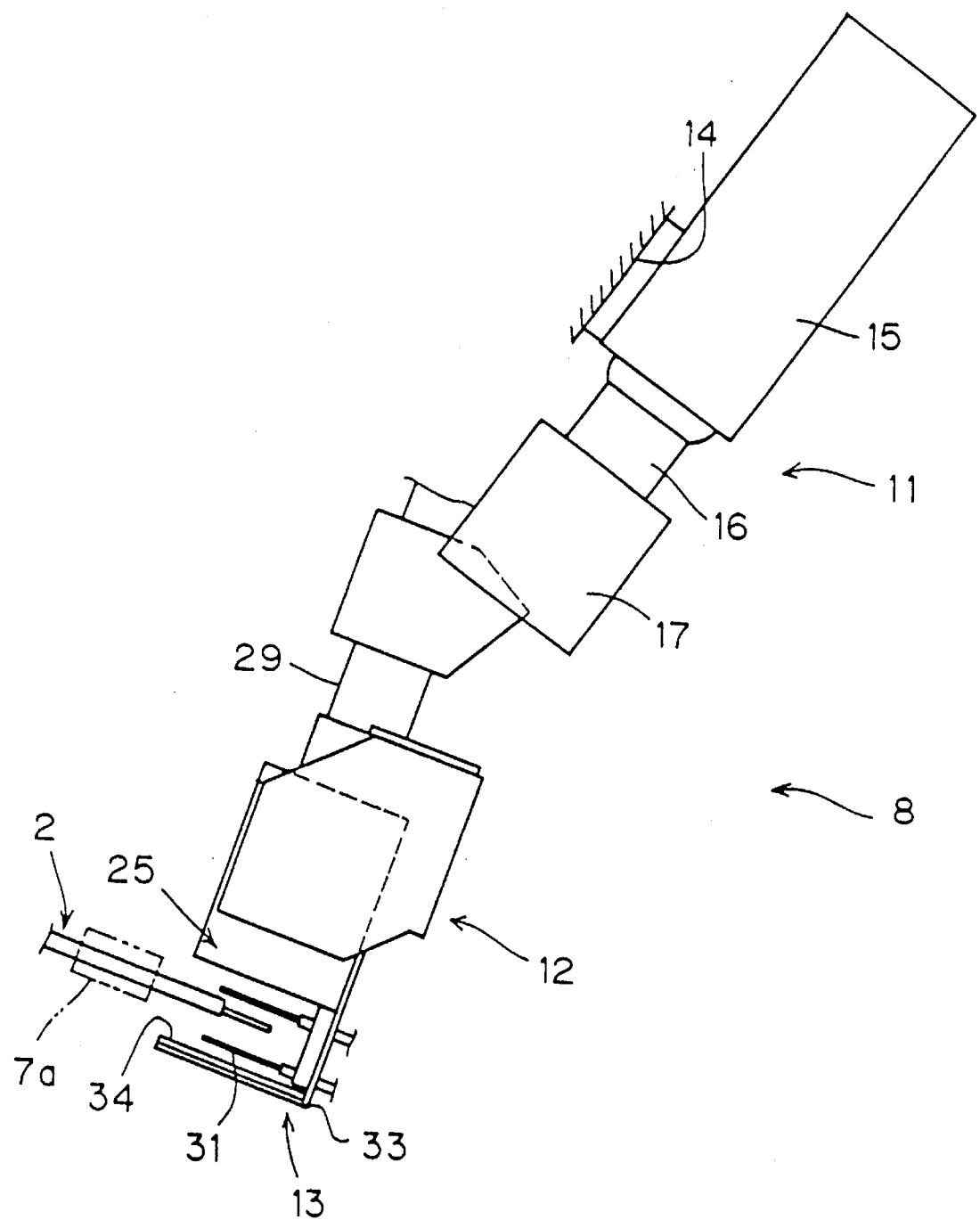
FIG. 3 is a view in the direction of the arrows III—III of FIG. 2.

Each of the sensors 31, 32 includes a light projector and a light receiver which are spaced apart in the direction of the optical axis O on opposite sides of the bidirectional path P as shown in FIGS. 2 to 4.

Figure 7:
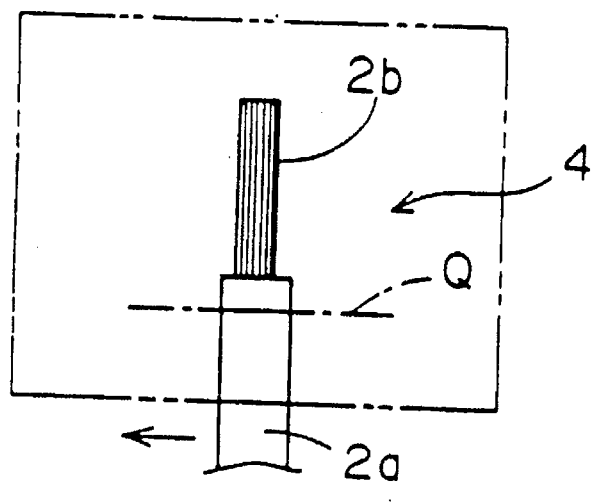
FIG. 7 illustrates a photographed image of a cable end transported in a first direction.
Figure 8:
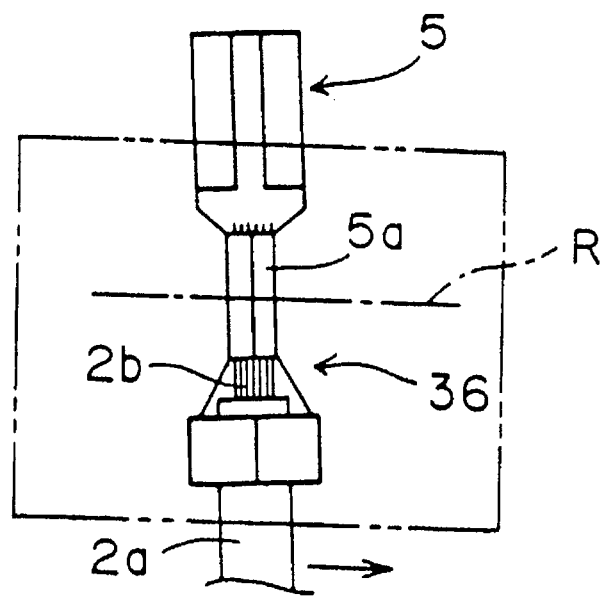
FIG. 8 illustrates a photographed image of a cable end transported in a second direction.

A detecting position Q of the first sensor 31 is located in corresponding relation to the passing position of the end of the coating 2a of the stripped cable 2 as shown in FIG. 7, and a detecting position R of the second sensor 32 is located in corresponding relation to the passing position of an intermediate part of a core barrel part 5a serving as a core crimping part for crimping the crimp terminal 5 to a core part 2b as shown in FIG. 8. The photographing range of the image pickup camera 11 is shown in phantom in FIGS. 7 and 8.

An irregular reflector plate 34 serving as a sub-illuminating means is mounted over the bottom surface of the sensor mounting bracket 33 opposed to the illuminating portions 20 to direct illumination in the direction opposite from the illuminating portions 20 toward the end of the cable 2 passing therethrough along the bidirectional path P. The optical axis O of the image pickup camera 11 is slightly inclined toward the end surface at the end of the cable 2 from the direction orthogonal to the longitudinal direction of the cable 2 passing through the photographing position for ease of recognition as shown in FIG. 5.

FIGS. 9, 10A, 10B, 11 through 32 illustrate illuminance distribution caused by the interference of illuminated light. The light sources are considered as surface light sources because of the function of the transmitted light scattering plates 27 of the illuminating portions 20. The points at which the two lines from the opposite ends of each of the transmitted light scattering plates 27 serving as the light sources form the same angle are plotted to form a curve on which a substantially uniform illuminance is provided.

Figure 9:
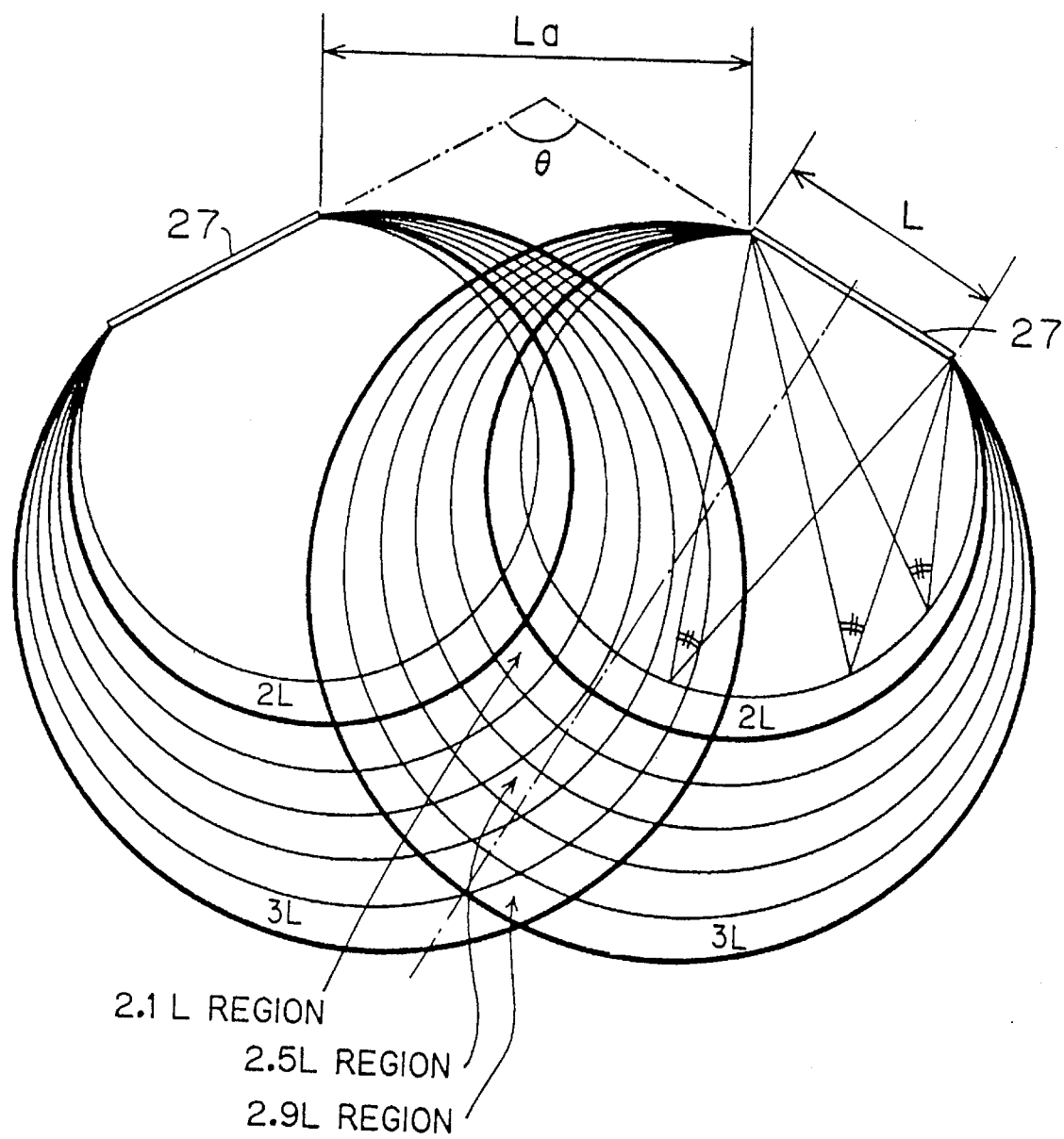
FIG. 9 illustrates illuminance distribution caused by the interference of illuminated light.

Referring to FIG. 9, with the width L of the transmitted light scattering plates 27 of the illuminating portions 20 used as a reference, curves each indicative of a substantially uniform illuminance are drawn so that they are spaced 0.2 L apart on the perpendicular bisector of the width L of each transmitted light scattering plate 27 to produce an illuminance distribution chart. The region surrounded by the curves which are 2.0 L and 2.2 L apart from the pair of transmitted light scattering plates 27 is defined as a 2.1 L region, the region surrounded by the curves which are 2.4 L and 2.6 L apart therefrom is defined as a 2.5 L region, and the region surrounded by the curves which are 2.8 L and 3.0 L apart therefrom is defined as a 2.9 L region. Referring to FIGS. 10A and 10B, where $\Delta X$ and $\Delta Y$ denote the horizontal and vertical lengths of the regions, respectively, the effective approximate area $\Delta A$ of the regions is represented as $\Delta X \times \Delta Y/2$ and the ratio $\Delta R$ of the horizontal length to the vertical length is represented as $\Delta X/\Delta Y$.

FIGS. 11 through 27 are illuminance distribution charts with variation in spacing La between the pair of transmitted light scattering plates 27 and variation in interior angle formed by the pair of transmitted light scattering plates 27, assuming that the unit L of the reference length is 100. FIGS. 28 through 32 illustrate the relation between the values $\Delta X$, $\Delta Y$, $\Delta R$, $\Delta A$ and the angle $\theta$ for the respective regions.

Figure 11:
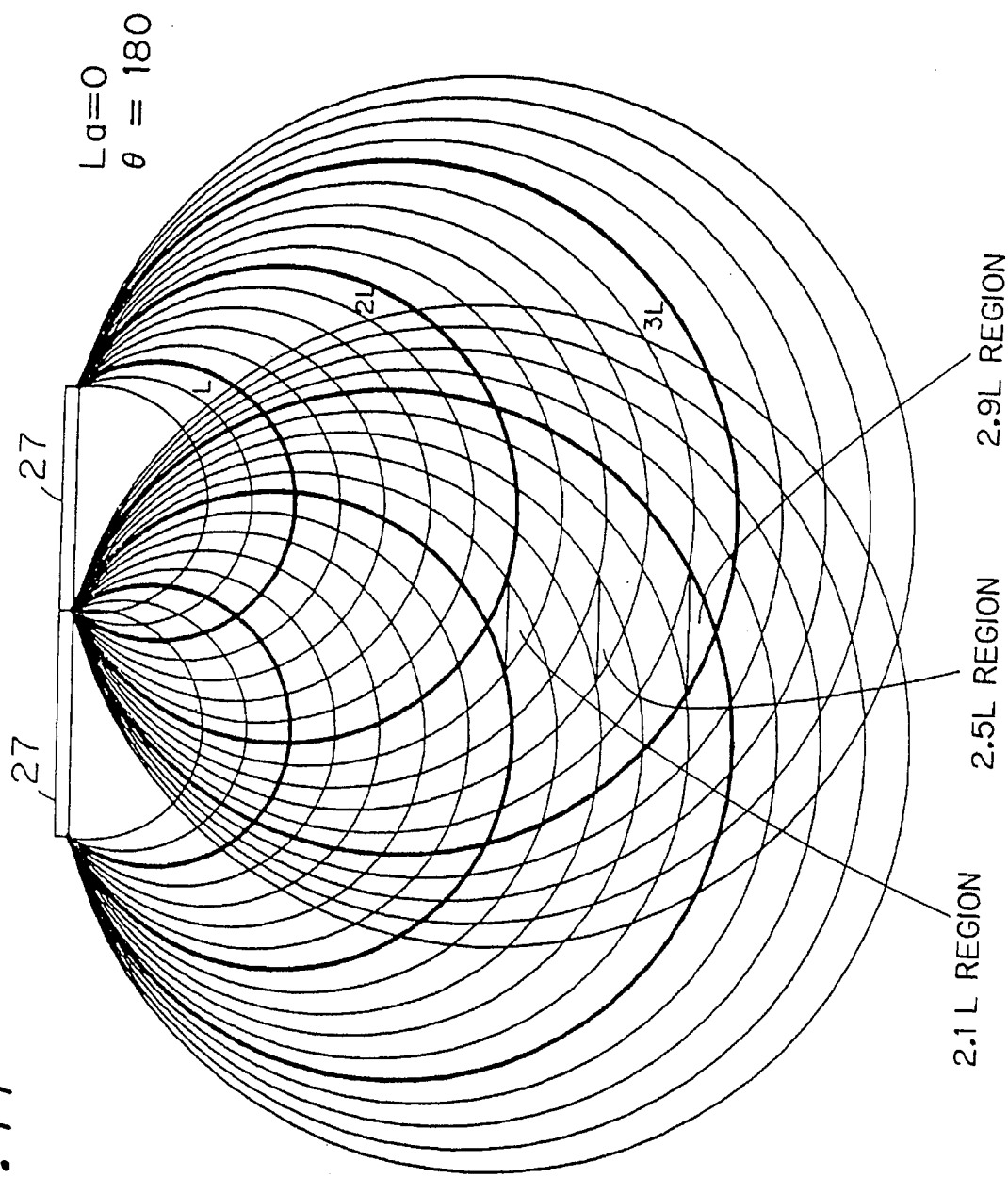
FIGS. 11 through 27 illustrate particular illuminance distribution caused by the interference of illuminated light.
Figure 12:
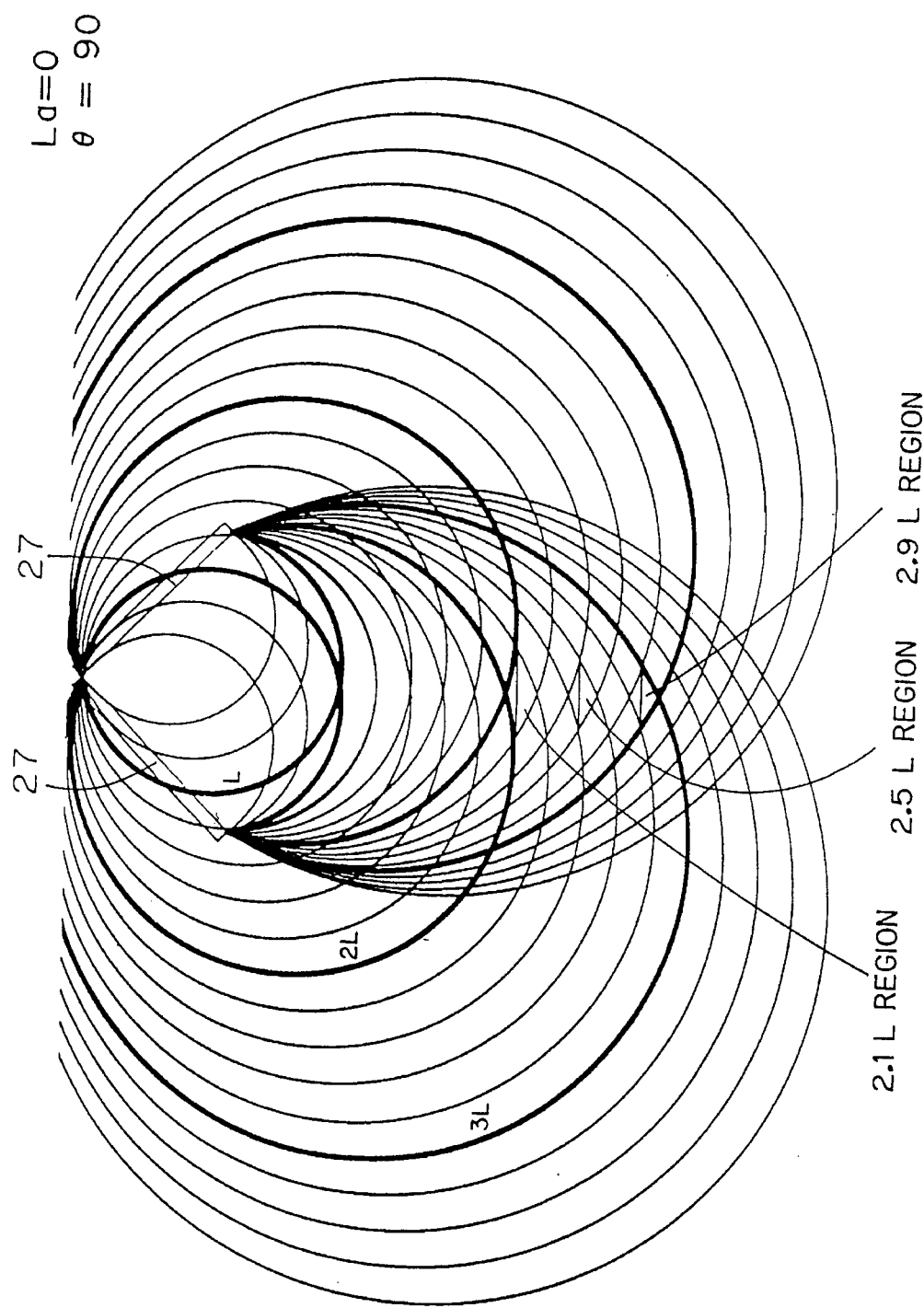
Figure 13:
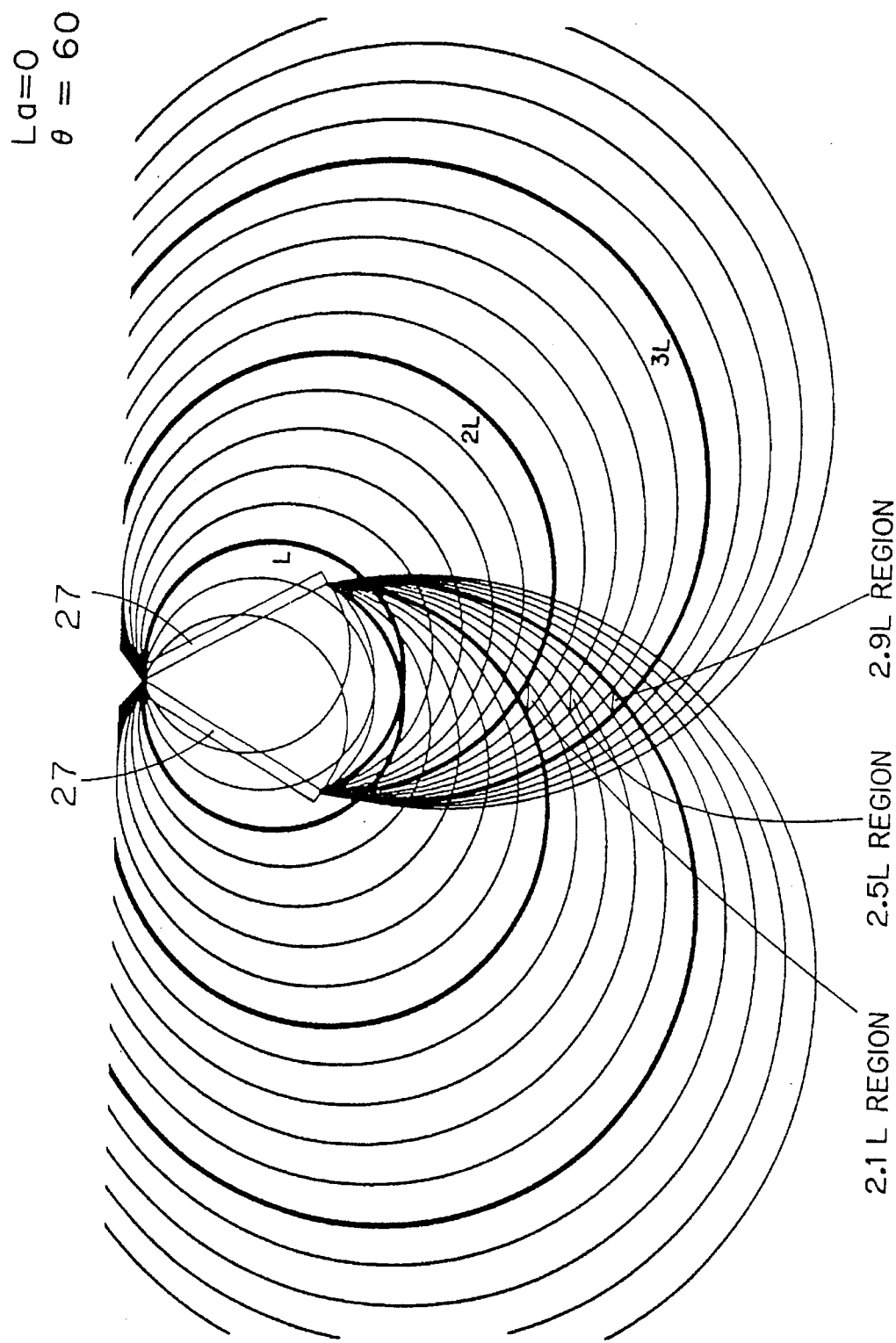
Figure 14:
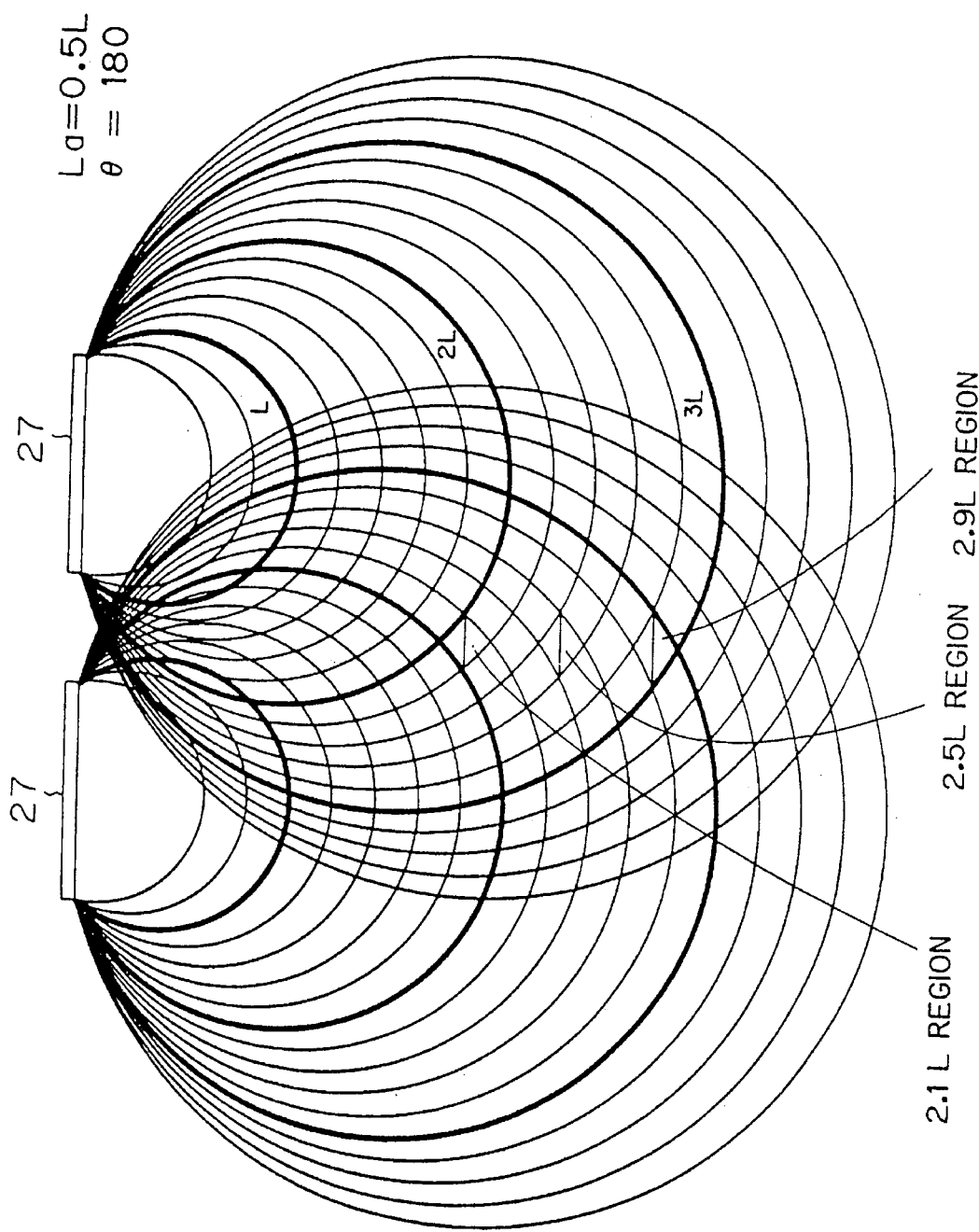
Figure 15:
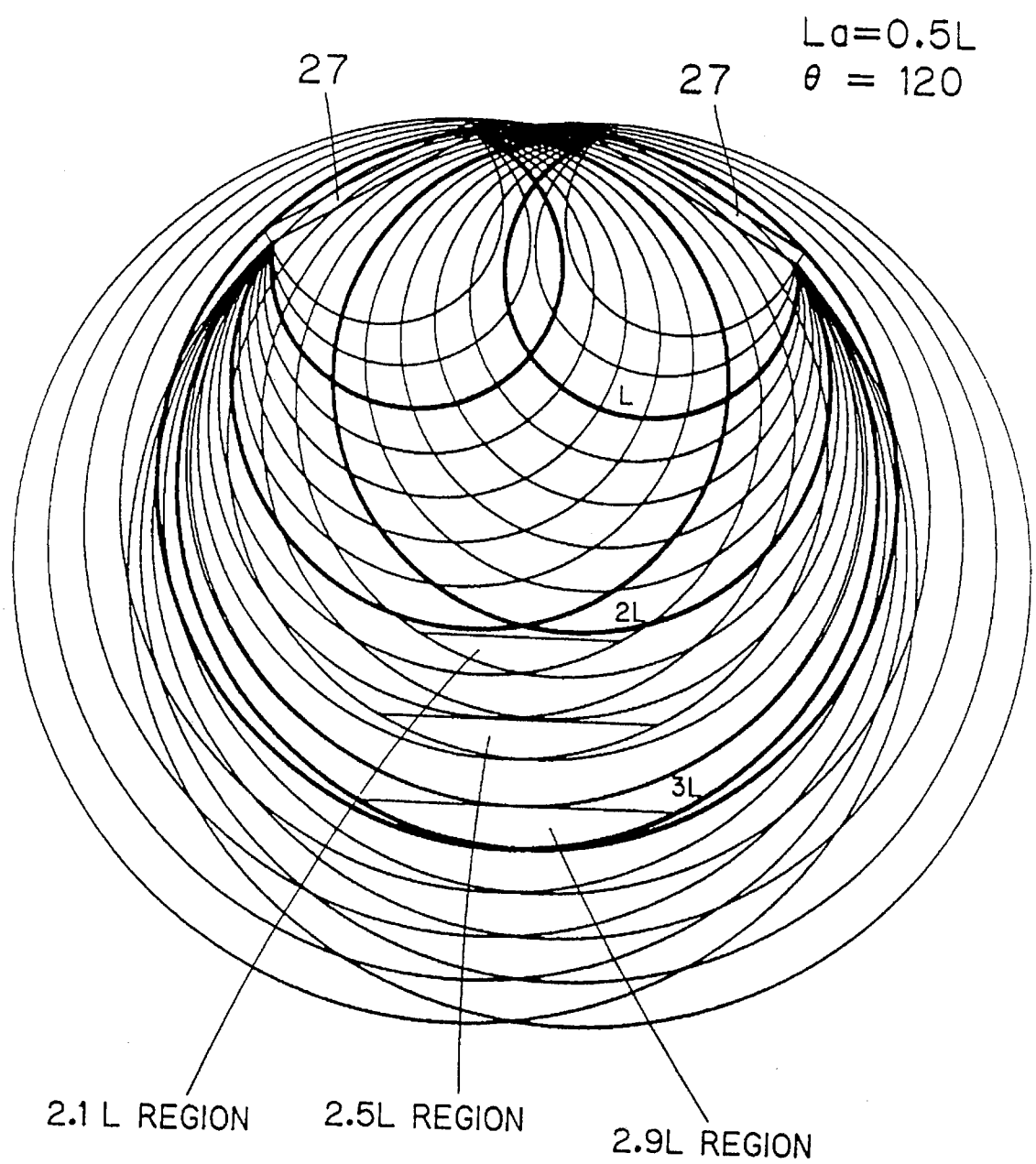
Figure 16:
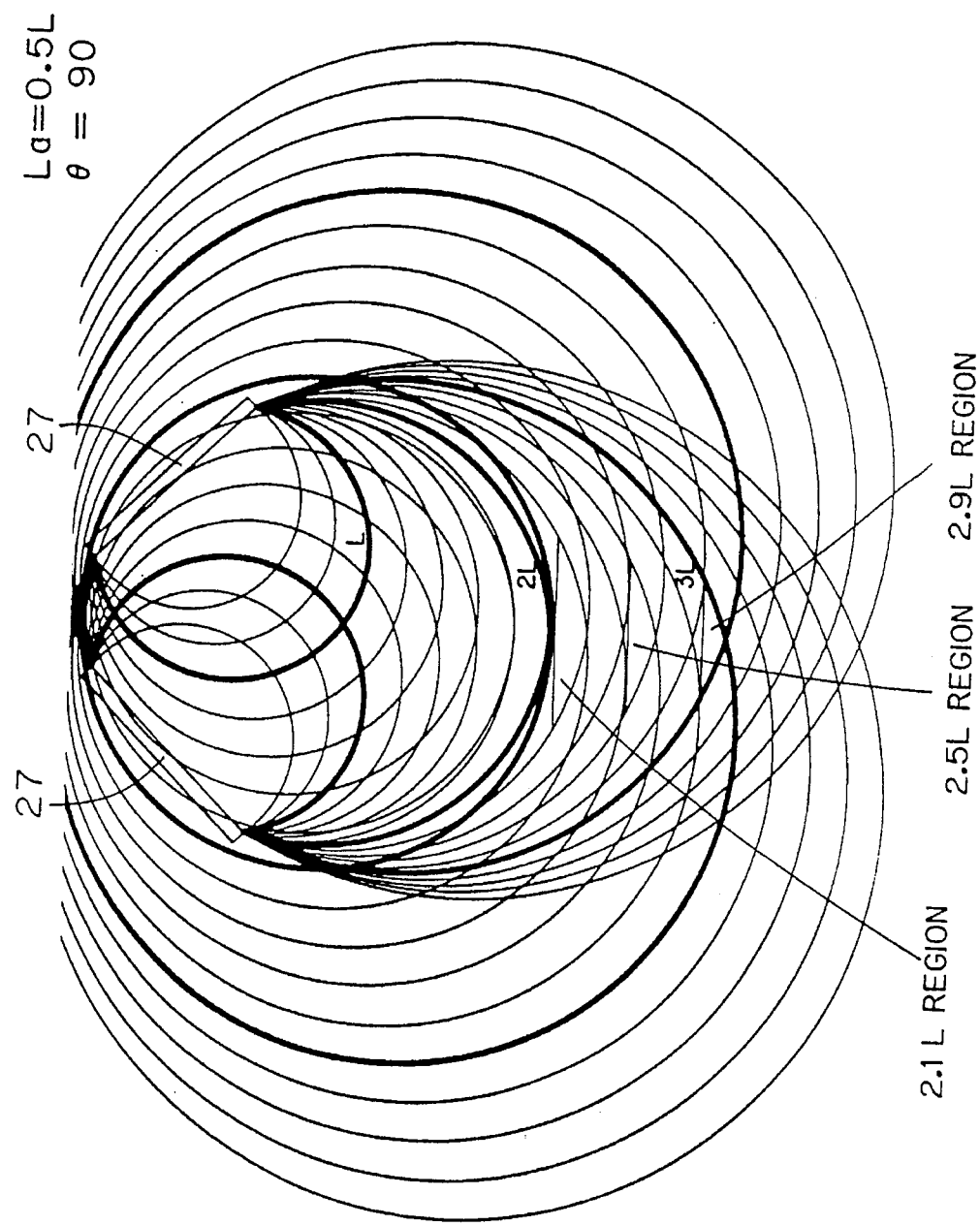
Figure 17:
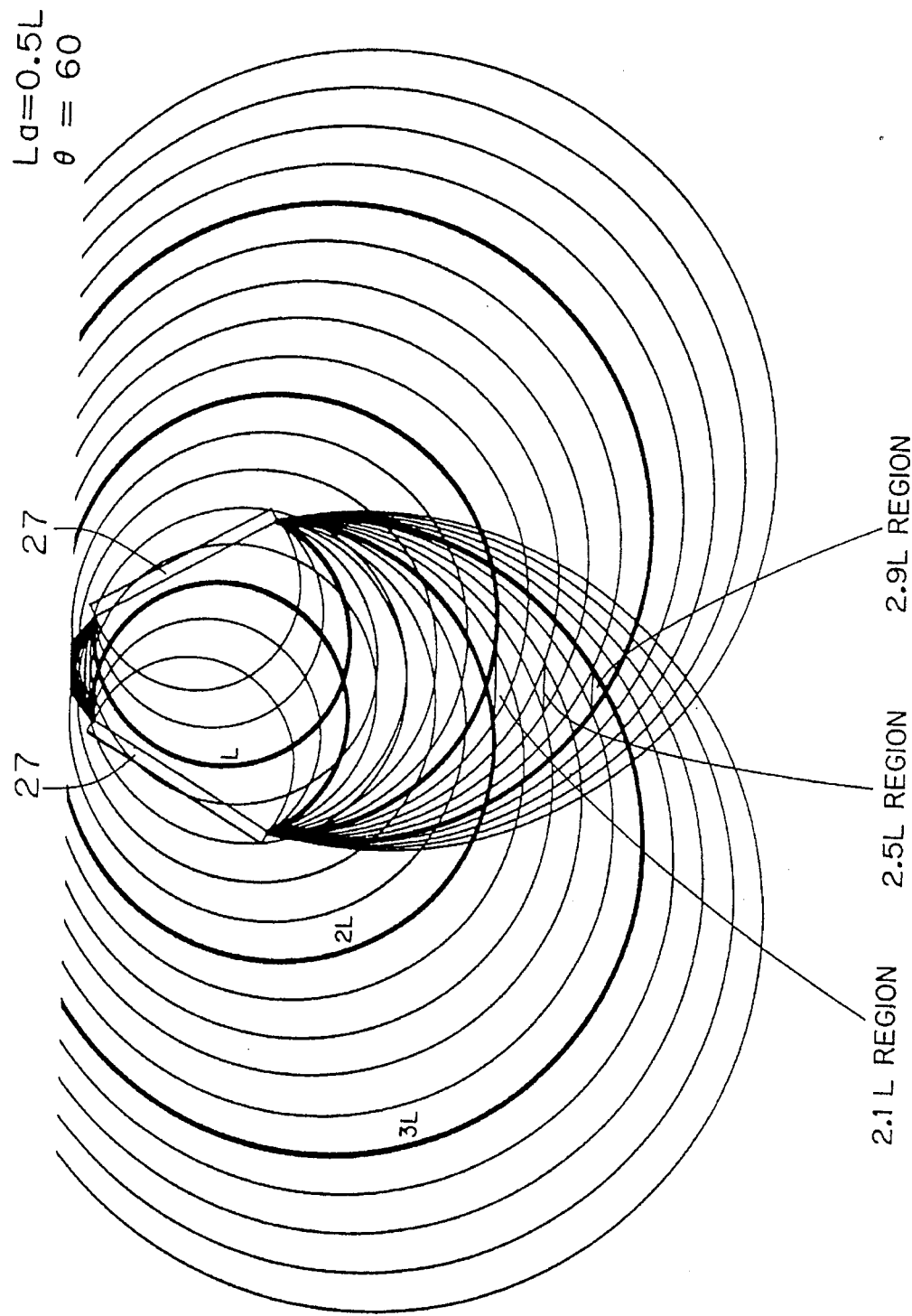
Figure 18:
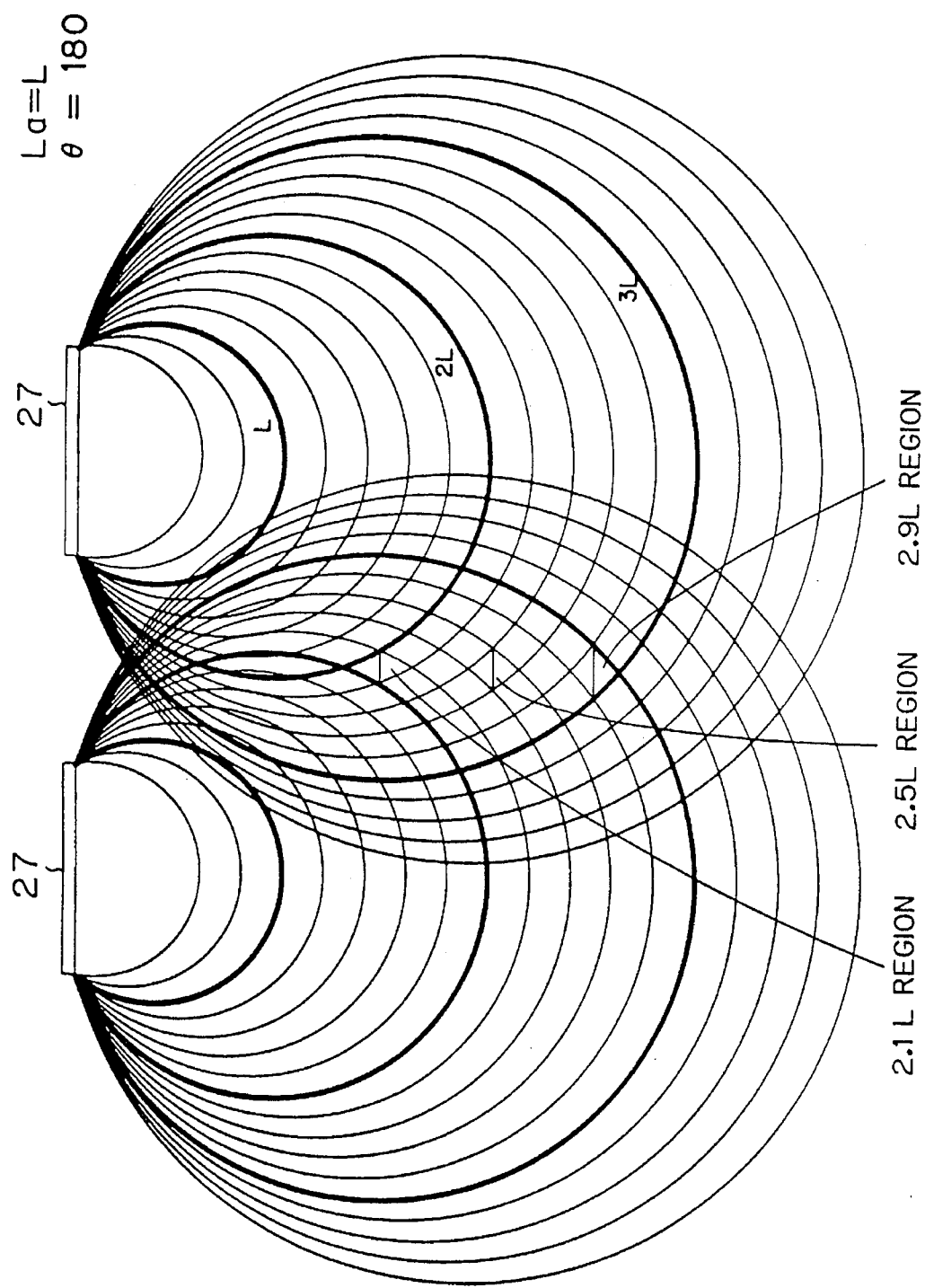
Figure 19:
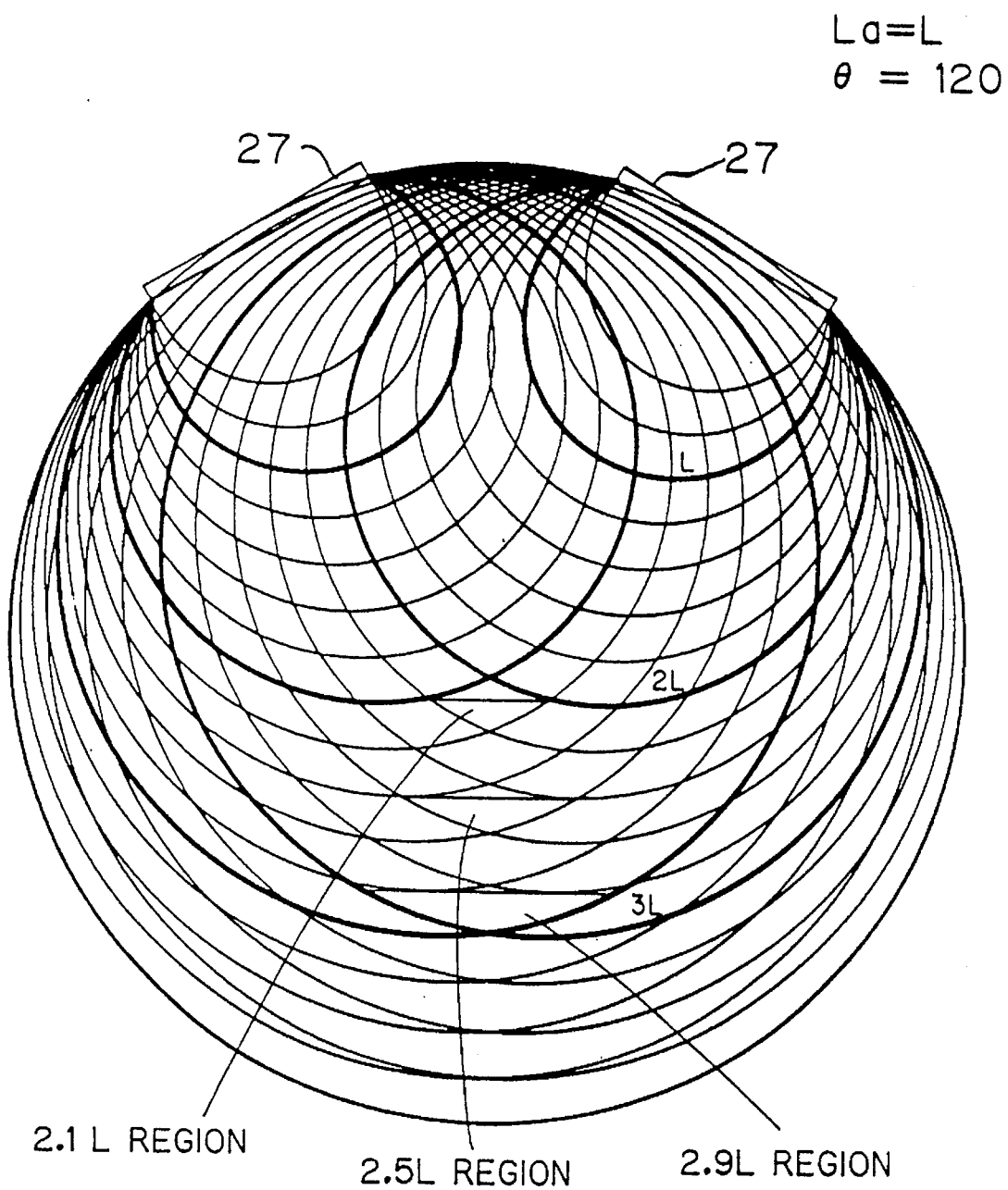
Figure 20:
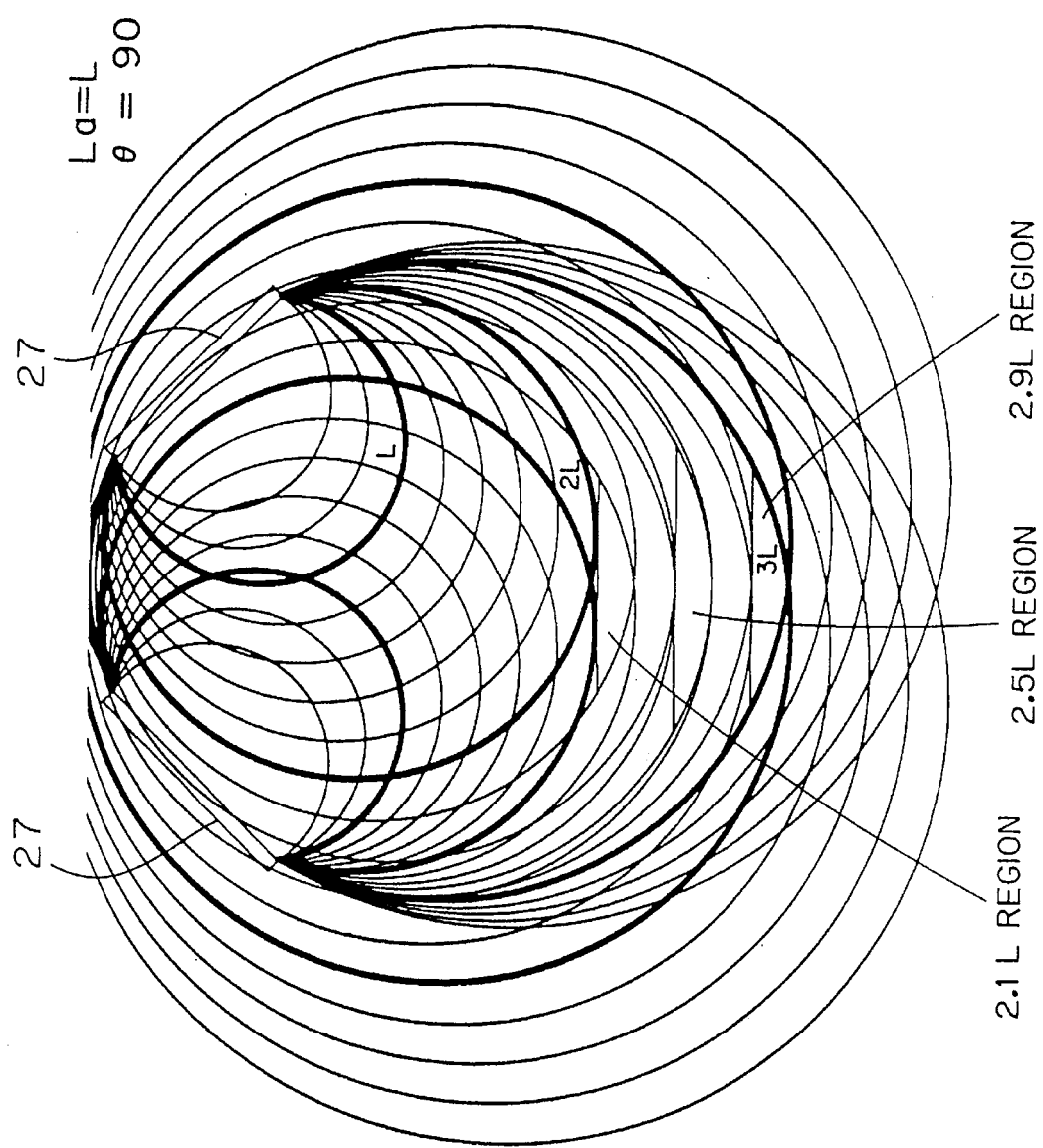
Figure 21:
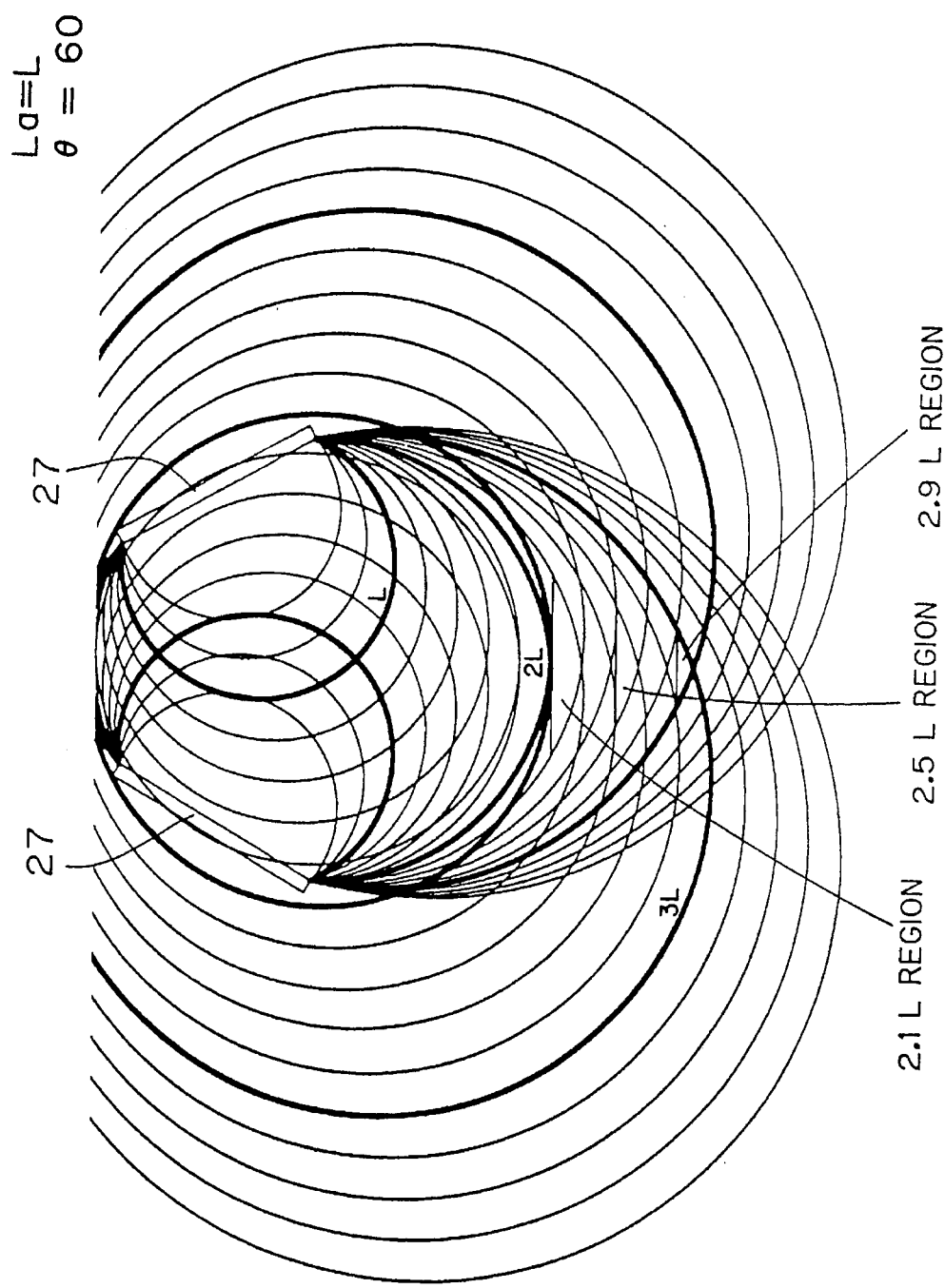
Figure 28:
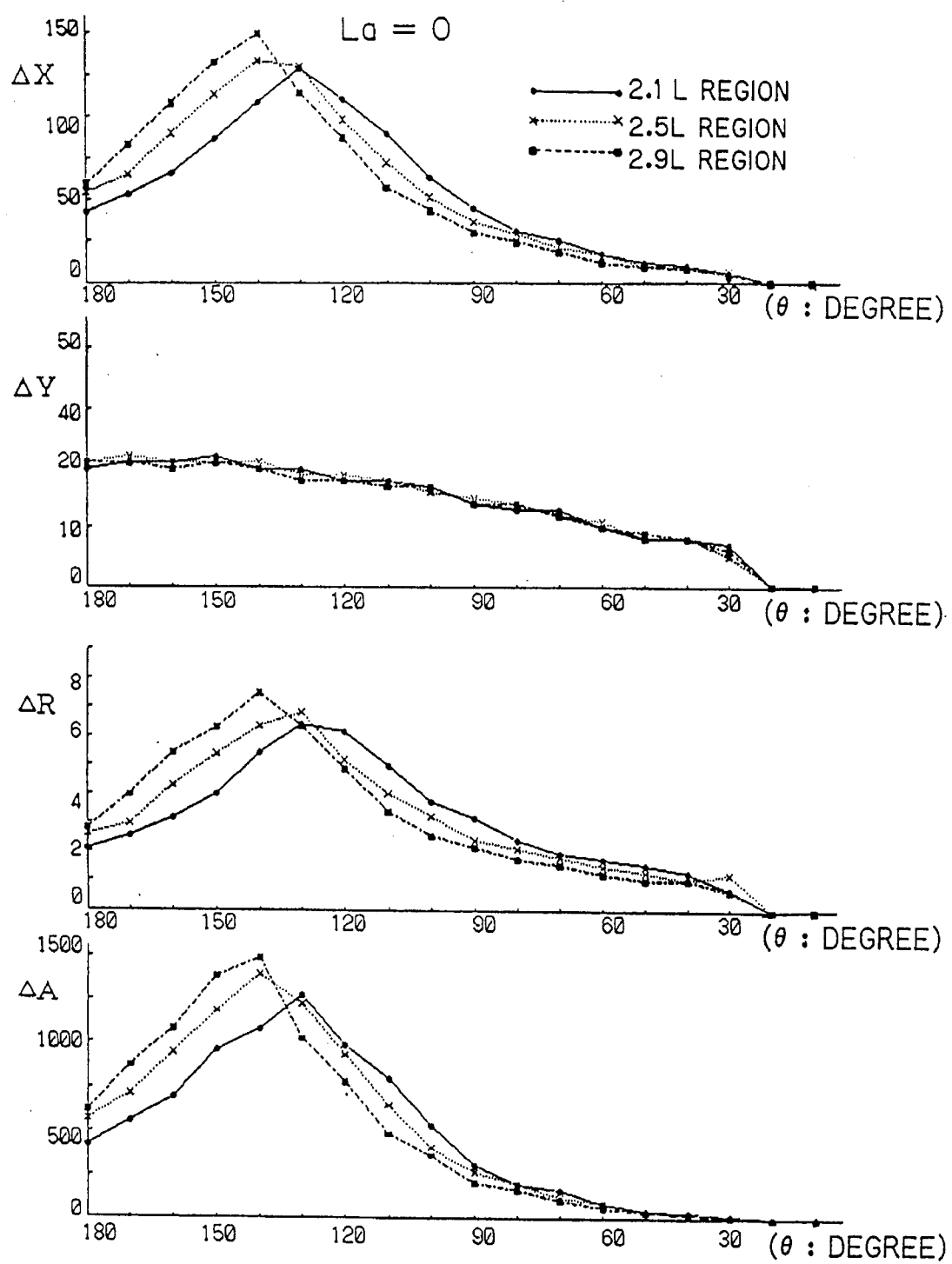
FIGS. 28 through 32 illustrate the relation between $\Delta X$, $\Delta Y$, $\Delta R$, $\Delta A$ and an angle $\theta$ for respective regions with variation in spacing between transmitted light scattering plates.

FIGS. 11 through 13 are illuminance distribution charts when the spacing La between the pair of transmitted light scattering plates 27 equals zero and the interior angle $\theta$ formed by the pair of transmitted light scattering plates 27 equals 180 degrees, 90 degrees, 60 degrees, respectively. FIG. 28 illustrates the relation between the values $\Delta X$, $\Delta Y$, $\Delta R$, $\Delta A$ and the angle $\theta$ when the spacing La equals zero.

Figure 29:
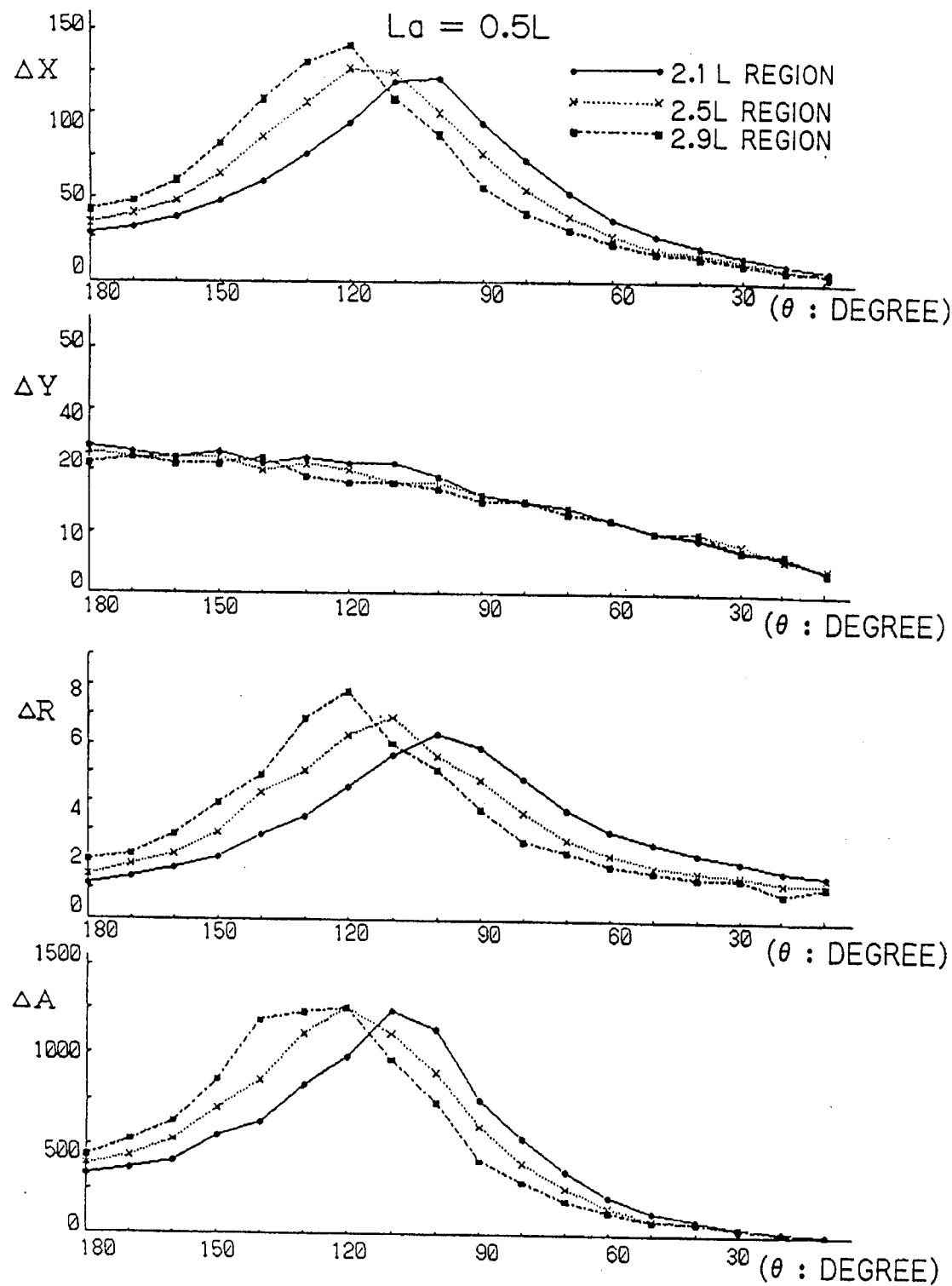

FIGS. 14 through 17 are illuminance distribution charts when the spacing La between the pair of transmitted light scattering plates 27 equals 0.5 L and the interior angle $\theta$ formed by the pair of transmitted light scattering plates 27 equals 180 degrees, 120 degrees, 90 degrees, 60 degrees, respectively. FIG. 29 illustrates the relation between the values $\Delta X$, $\Delta Y$, $\Delta R$, $\Delta A$ and the angle $\theta$ when the spacing La equals 0.5 L.

Figure 30:
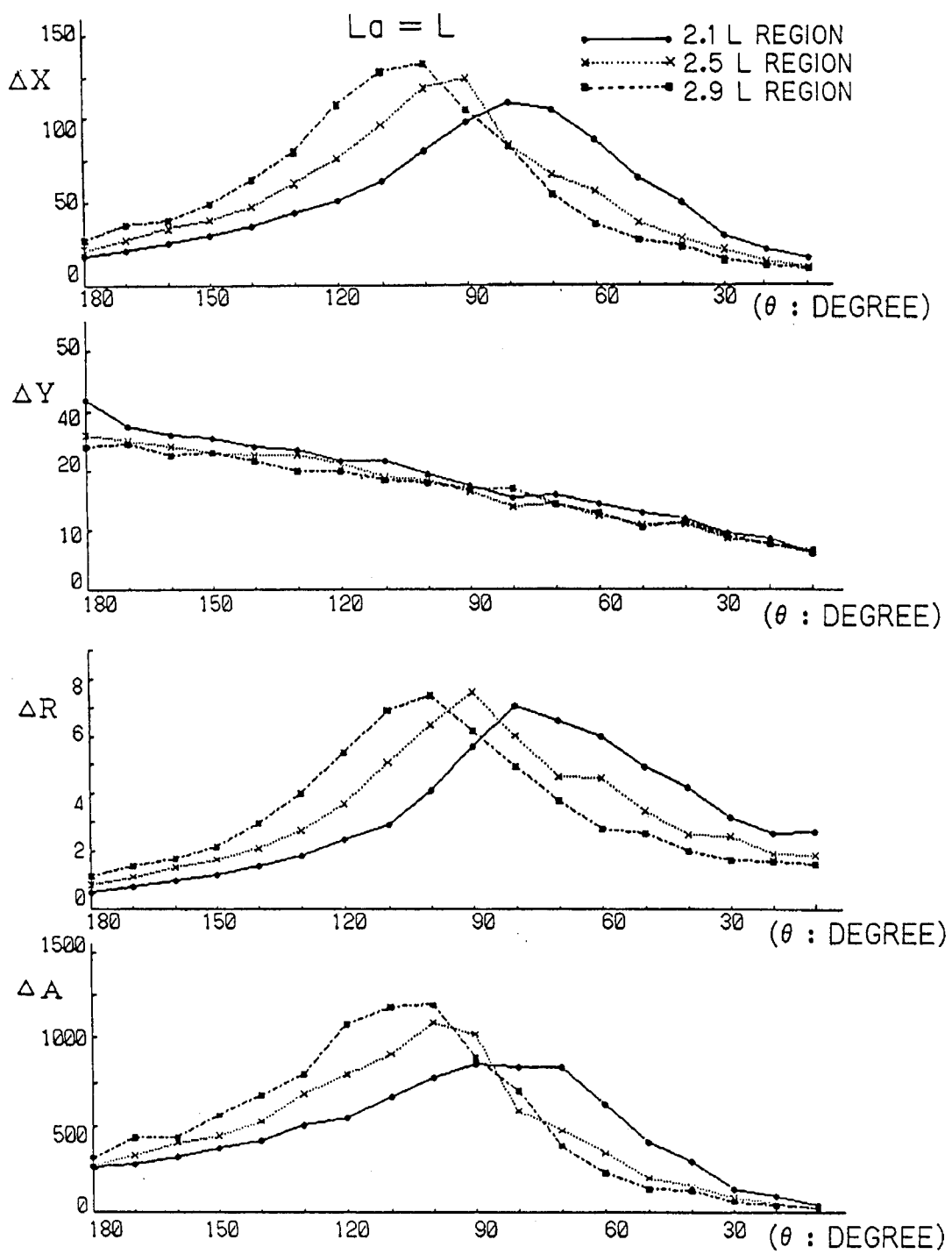

FIGS. 18 through 21 are illuminance distribution charts when the spacing La between the pair of transmitted light scattering plates 27 equals L and the interior angle $\theta$ formed by the pair of transmitted light scattering plates 27 equals 180 degrees, 120 degrees, 90 degrees, 60 degrees, respectively. FIG. 30 illustrates the relation between the values $\Delta X$, $\Delta Y$, $\Delta R$, $\Delta A$ and the angle $\theta$ when the spacing La equals L.

Figure 22:
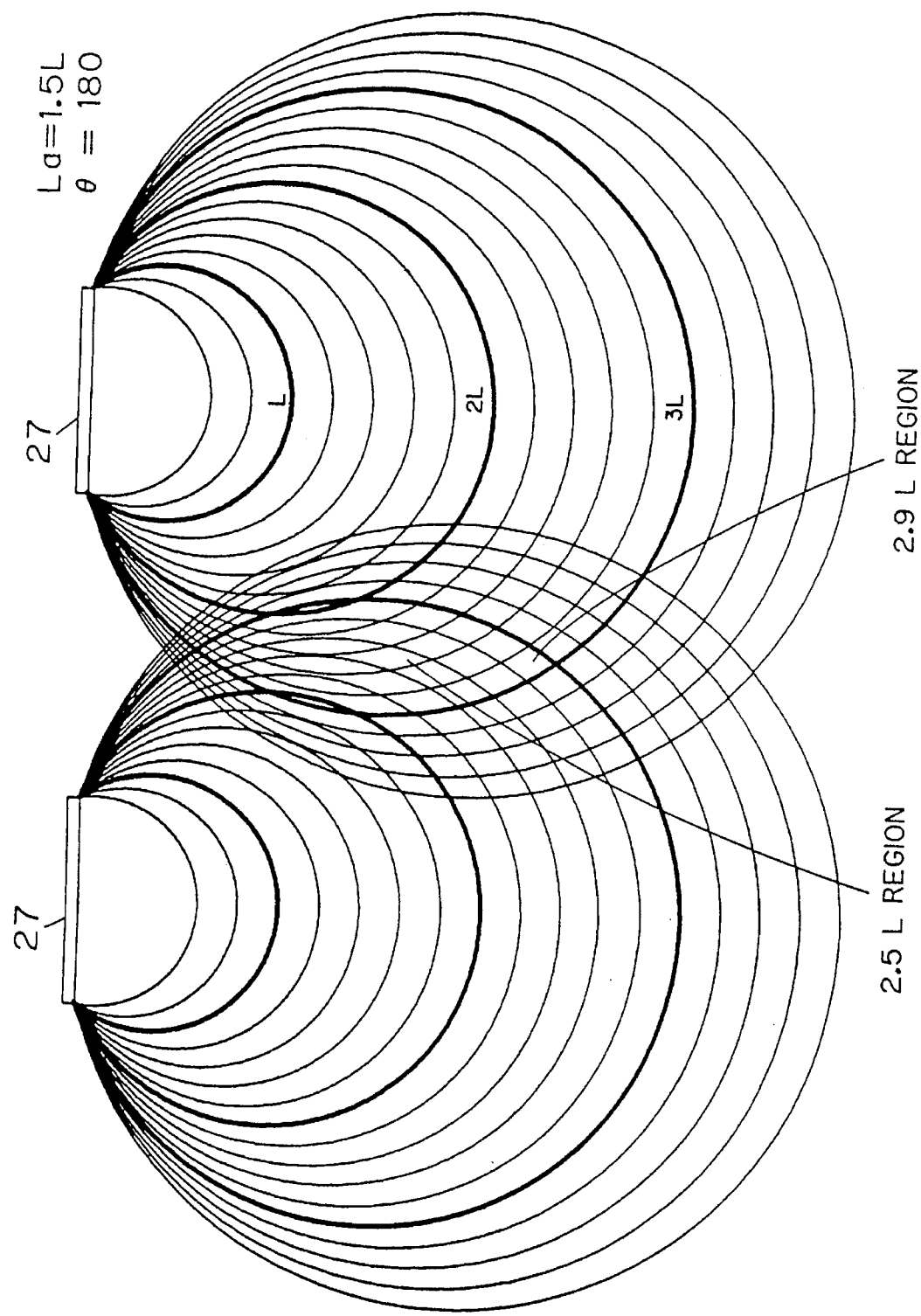
Figure 23:
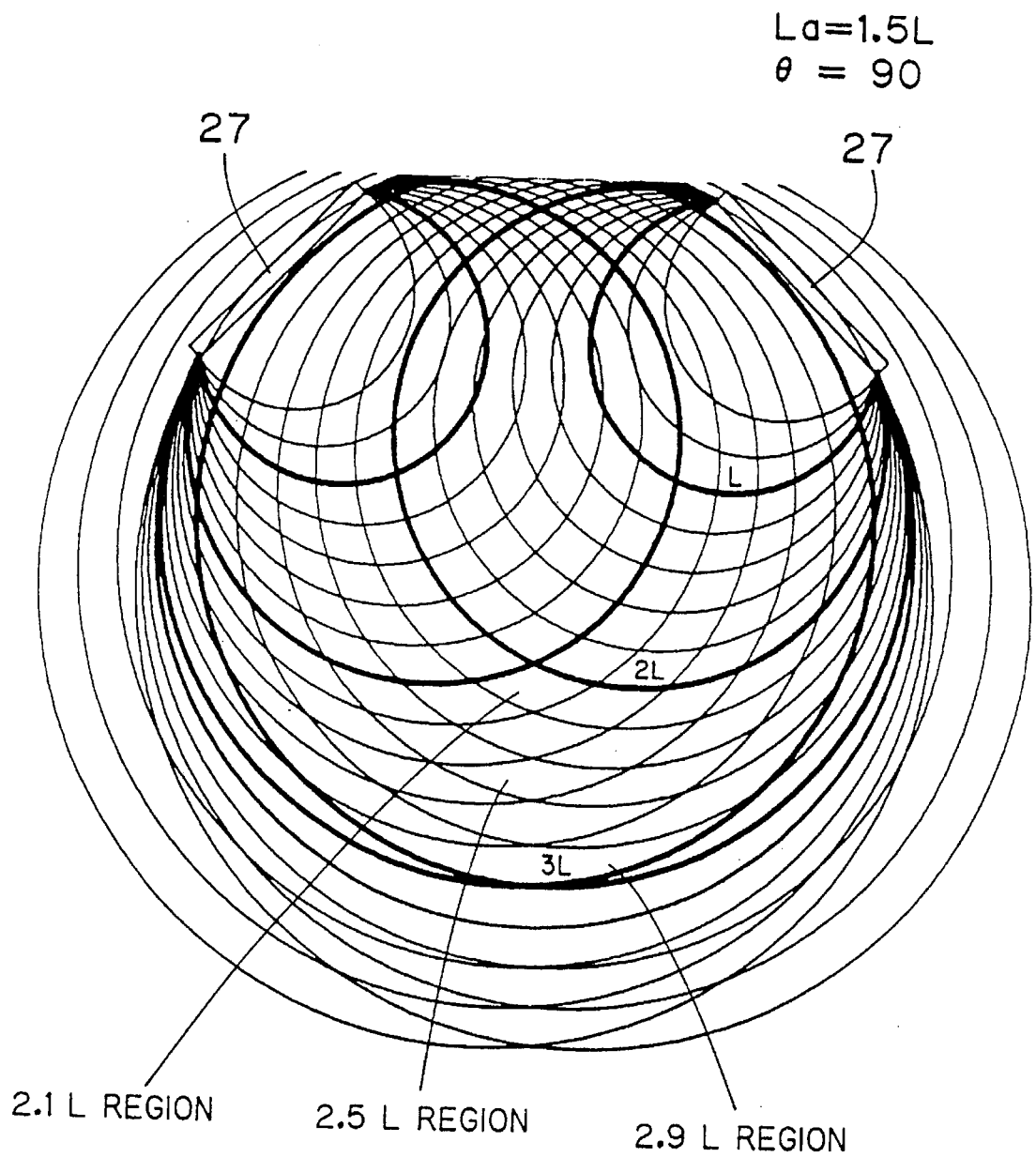
Figure 24:
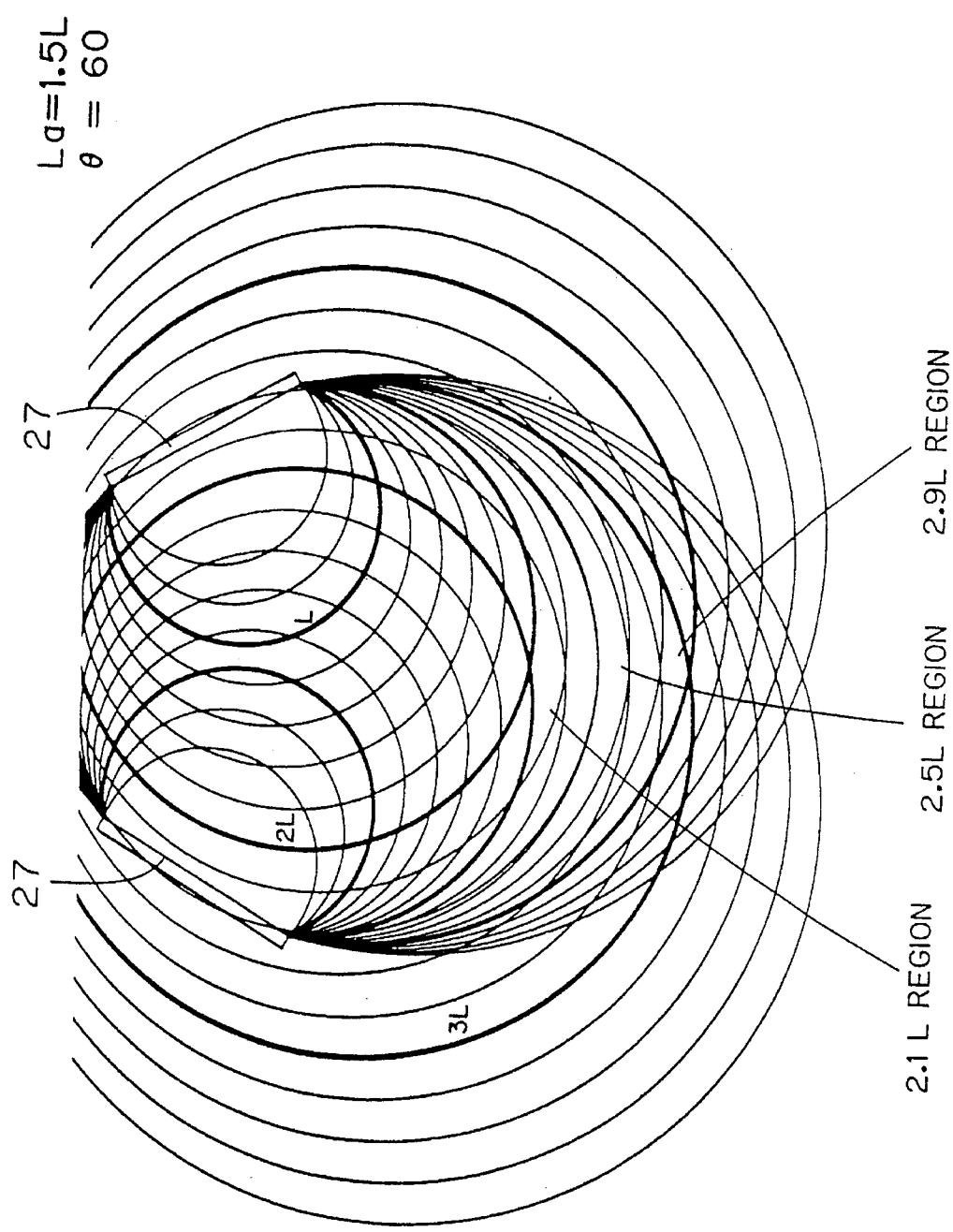
Figure 31:
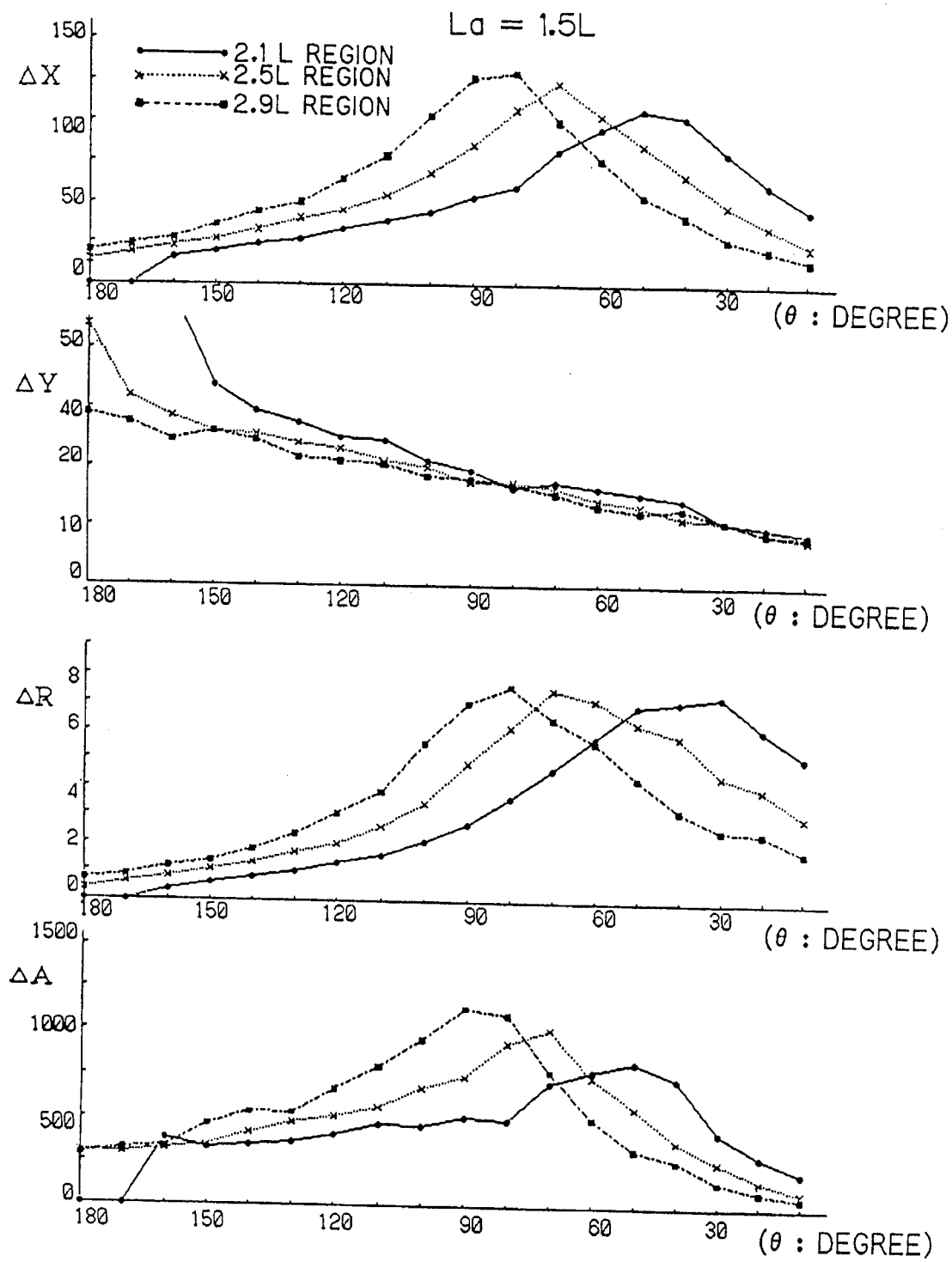

FIGS. 22 through 24 are illuminance distribution charts when the spacing La between the pair of transmitted light scattering plates 27 equals 1.5 L and the interior angle $\theta$ formed by the pair of transmitted light scattering plates 27 equals 180 degrees, 90 degrees, 60 degrees, respectively. FIG. 31 illustrates the relation between the values $\Delta X$, $\Delta Y$, $\Delta R$, $\Delta A$ and the angle $\theta$ when the spacing La equals 1.5 L.

Figure 25:
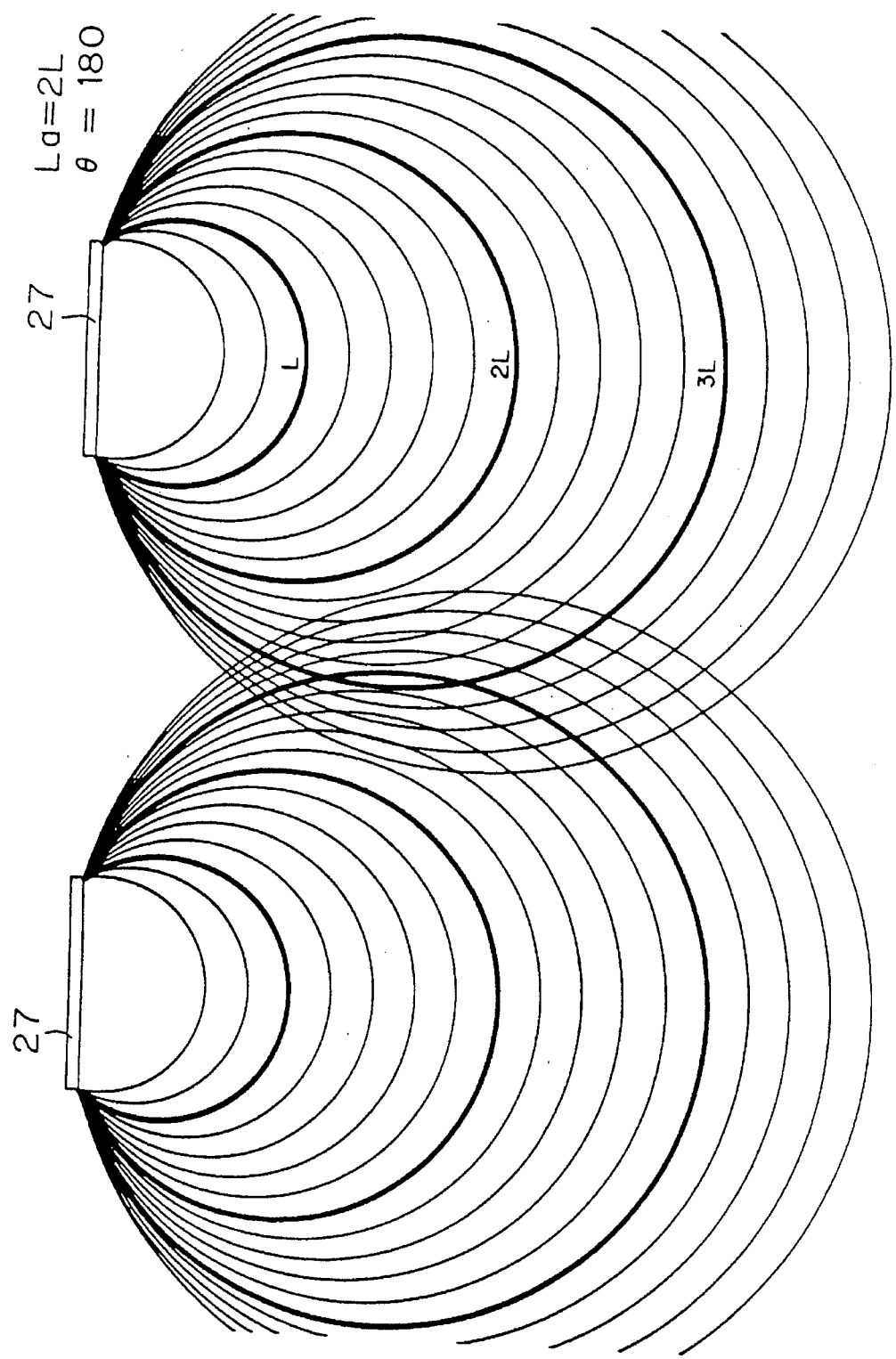
Figure 26:
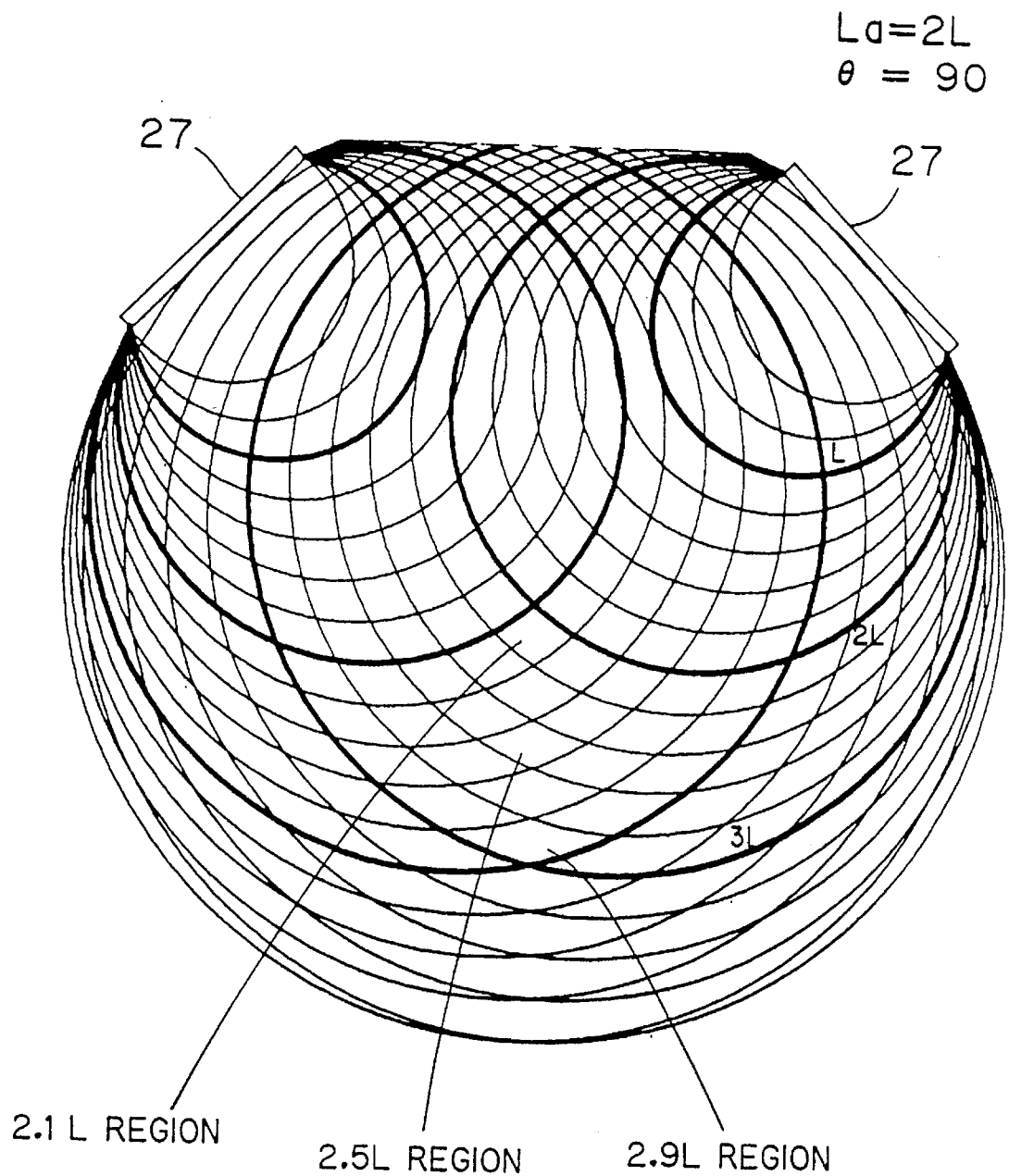
Figure 27:
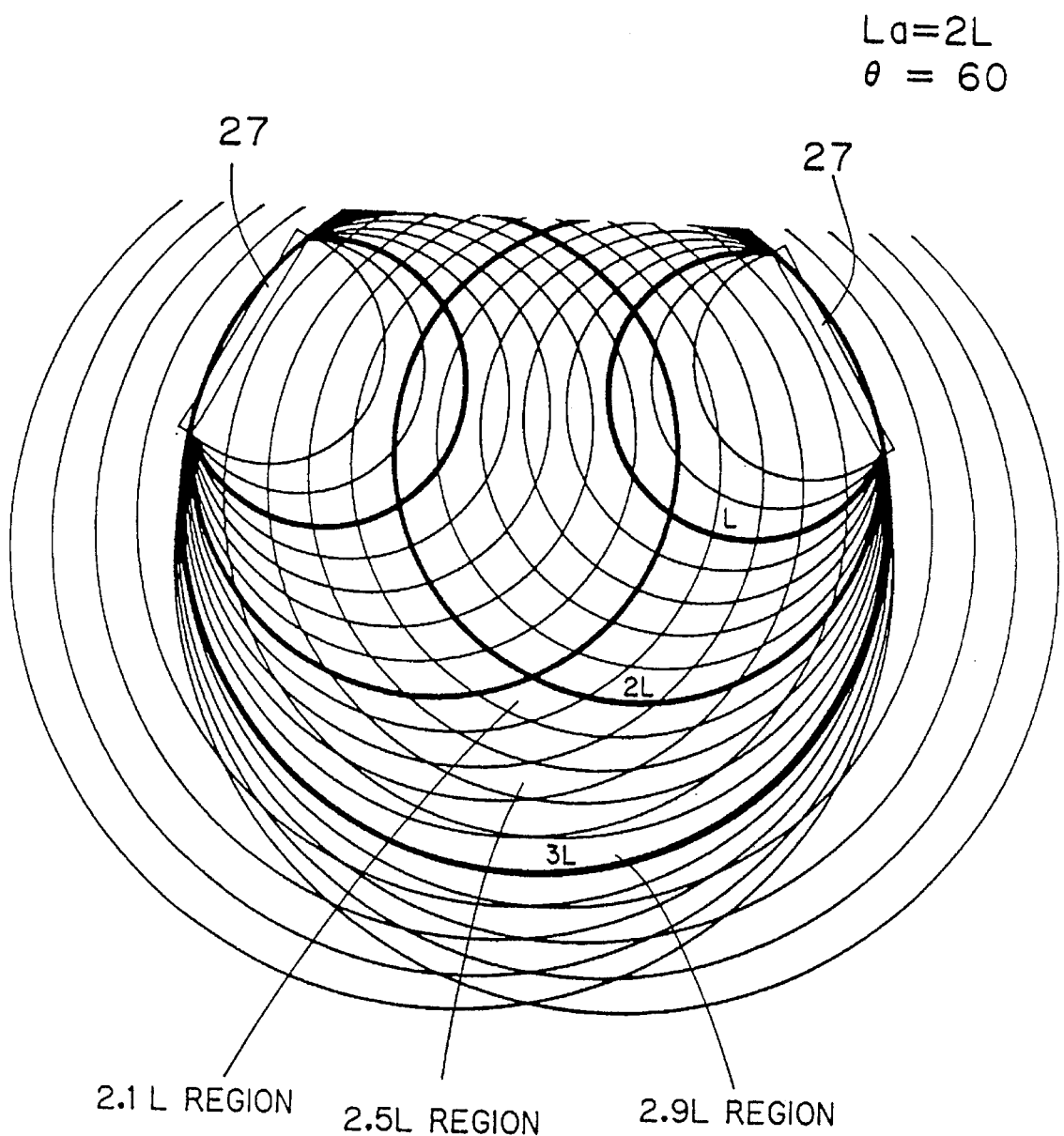
Figure 32:
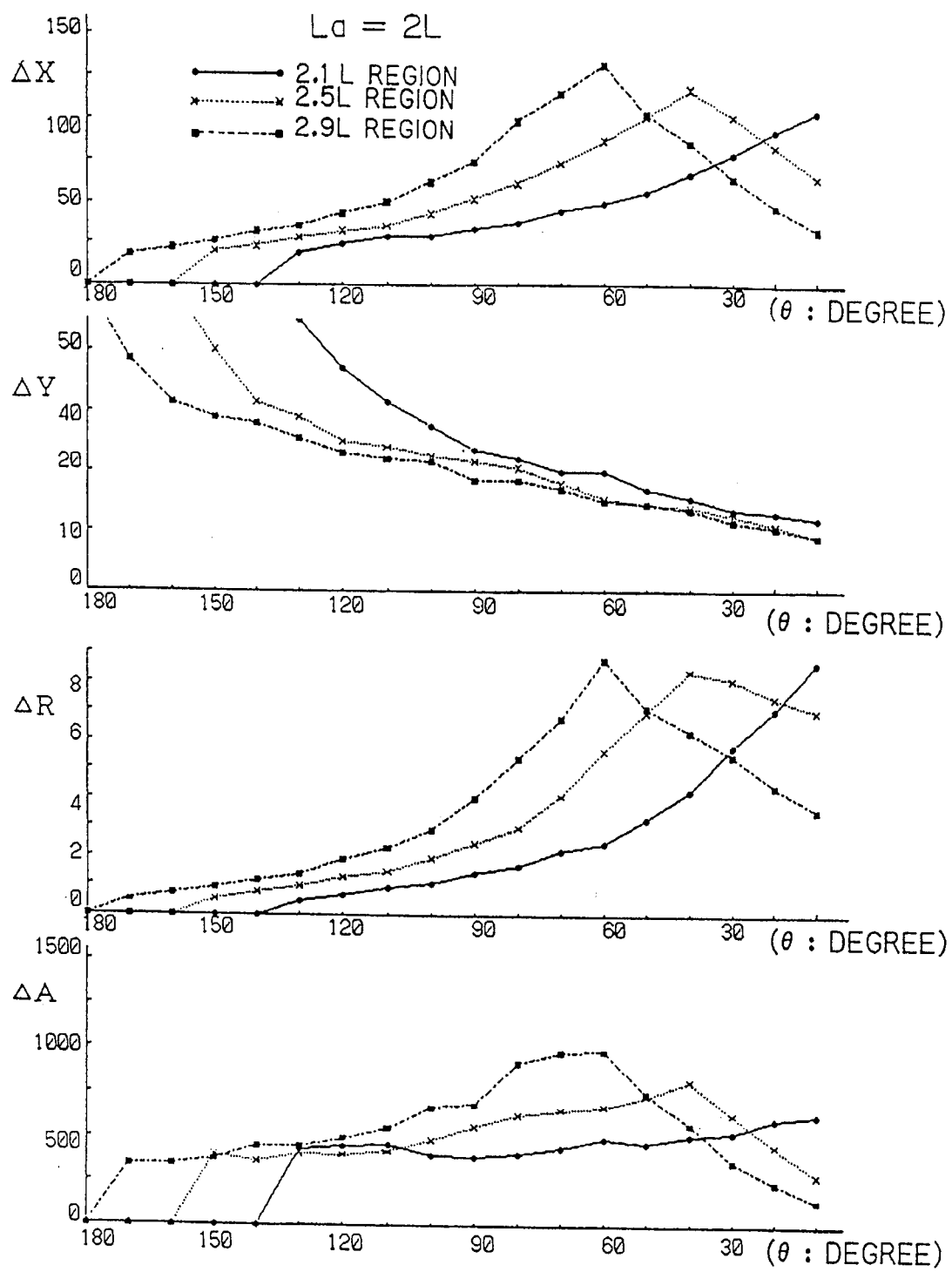

FIGS. 25 through 27 are illuminance distribution charts when the spacing La between the pair of transmitted light scattering plates 27 equals 2 L and the interior angle $\theta$ formed by the pair of transmitted light scattering plates 27 equals 180 degrees, 90 degrees, 60 degrees, respectively. FIG. 32 illustrates the relation between the values $\Delta X$, $\Delta Y$, $\Delta R$, $\Delta A$ and the angle $\theta$ when the spacing La equals 2 L.

With the spacing La=0 between the pair of transmitted light scattering plates 27 as shown in FIG. 28, the effective approximate area $\Delta A$ having a substantially uniform illuminance, the horizontal length $\Delta X$ along the bidirectional path P, and the ratio $\Delta R$ of the horizontal length $\Delta X$ to the vertical length $\Delta Y$ are maximum when the interior angle $\theta$ formed by the transmitted light scattering plates 27 ranges from about 120 to about 160 degrees.

With the spacing La=0.5 L between the pair of light scattering plates 27 as shown in FIG. 29, the effective approximate area $\Delta A$ having a substantially uniform illuminance, the horizontal length $\Delta X$ along the bidirectional path P, and the ratio $\Delta R$ of the horizontal length $\Delta X$ to the vertical length $\Delta Y$ are maximum when the interior angle $\theta$ formed by the transmitted light scattering plates 27 ranges from about 90 to about 150 degrees.

With the spacing La=L between the pair of transmitted light scattering plates 27 as shown in FIG. 30, the effective approximate area $\Delta A$ having a substantially uniform illuminance, the horizontal length $\Delta X$ along the bidirectional path P, and the ratio $\Delta R$ of the horizontal length $\Delta X$ to the vertical length $\Delta Y$ are maximum when the interior angle $\theta$ formed by the transmitted light scattering plates 27 ranges from about 70 to about 130 degrees.

With the spacing La=1.5 L between the pair of transmitted light scattering plates 27 as shown in FIG. 31, the effective approximate area $\Delta A$ having a substantially uniform illuminance, the horizontal length $\Delta X$ along the bidirectional path P, and the ratio $\Delta R$ of the horizontal length $\Delta X$ to the vertical length $\Delta Y$ are maximum when the interior angle $\theta$ formed by the transmitted light scattering plates 27 ranges from about 40 to about 110 degrees.

With the spacing La =2 L between the pair of transmitted light scattering plates 27 as shown in FIG. 32, the effective approximate area $\Delta A$ having a substantially uniform illuminance, the horizontal length $\Delta X$ along the bidirectional path P, and the ratio $\Delta R$ of the horizontal length $\Delta X$ to the vertical length $\Delta Y$ are maximum when the interior angle $\theta$ formed by the transmitted light scattering plates 27 ranges from about 30 to about 90 degrees.

It will be understood from the graphs of FIGS. 28 through 32 that the range of the interior angle $\theta$ formed by the transmitted light scattering plates 27 in corresponding relation to the maximum effective approximate area $\Delta X$ having a substantially uniform illuminance, the maximum horizontal length X along the bidirectional path P, and the maximum ratio $\Delta R$ of the horizontal length $\Delta X$ to the vertical length $\Delta Y$ is gradually shifted toward the smaller angle $\theta$ as the spacing La between the transmitted light scattering plates 27 increases.

Therefore, the angle $\theta a$ of inward inclination of the transmitted light scattering plates 27 which is suitable for photographing may be selected as required so as to provide the suitable effective approximate area $\Delta A$ and horizontal length $\Delta X$ of the region lying in the position along the bidirectional path P in accordance with the determined relation between the spacing between the transmitted light scattering plates 27 and the position of the bidirectional path P.

In the preferred embodiment of the present invention as above constructed, the end of the cable 2 fed from a cable feeding portion not shown to the cable clamp portion 7a of the transport arm 7 is held by the cable clamp portion 7a and subjected to the stripping of the coating 2a in the stripping portion 3.

Upon completion of the stripping, the transport arm 7 is pivoted on the support shaft 9 to transport the stripped part 4 at the end of the cable 2 in the first direction from an initial position of the bidirectional path P. In the course of the transport, the first sensor 31 detects the end of the cable 2 to actuate a timer, and the image pickup camera 11 is controlled so that the shutter fires when the stripped part 4 passes through the position of the optical axis O.

As the end of the cable 2 reaches the terminal crimping portion 6, the crimp terminal 5 is crimped to the stripped part 4. Upon completion of the crimping, the transport arm 7 is pivoted on the support shaft 9 to transport a terminal crimped part 36 at the end of the cable 2 in the second direction along the bidirectional path P from the terminal crimping portion 6. In the course of the transport, the second sensor 32 detects the end of the cable 2 to actuate the timer, and the image pickup camera 11 is controlled so that the shutter fires when the terminal crimped part 36 passes through the position of the optical axis O.

On arrival at the initial position in the stripping portion 3, the cable 2 is transported by a predetermined length in a predetermined direction and cut in position. The stripping and terminal crimping are repeatedly performed on successive cables 2 in sequential order in the same fashion, and the stripped part and terminal crimped part 36 of the successive cables 2 are photographed during the transport of the end thereof and subjected to the conventional image processing and judgement whether the stripping and crimping conditions are defective or not.

According to the preferred embodiment, as above stated, the illuminating portions 20 are provided on opposite sides of the photographing path 19 of the image pickup camera 11 to direct illumination in substantially the same direction as the photographing direction of the image pickup camera 11 toward the end of the cable 2 passing therethrough along the bidirectional path P, and each of the illuminating portions 20 is elongated in substantially the same direction as the longitudinal direction of the transported cable 2. The pair of illuminating portions 20 which are arranged to form the suitable angle θa direct illumination in inwardly angled directions from the opposite sides of the photographing path 19 of the image pickup camera 11 toward the end of the cable 2 passing along the bidirectional path P. Thus, the interference of the illuminated light emitted from the illuminating portions 20 ensures a stable illuminance over a wide range along the bidirectional path P.

Therefore, a sufficient illuminance for photographing the end of the cable 2 moved along the bidirectional path P is satisfactorily ensured when differences in photographing attitude and passing position along the bidirectional path P occur between the stripped end of the cable 2 moved in the first direction and the end of the cable 2 with the crimp terminal 5 crimped thereto and moved in the second direction and when the diameter of the cable 2 and the type of the crimp terminal 5 are varied. This allows the high-shutter-speed image pickup camera 11 to satisfactorily capture the reflected image of the end of the cable 2 moving at high speeds, thereby providing a great amount of image information and achieving inspection using more correct image information and improvement in inspection reliability.

Further, the light emitted from the light source in the lamp housing 21 located in a vacant spacing in the separate position is designed to be guided to the light projecting portions 23 of the illuminating portions 20 by the optical fibers 22, permitting the illuminating portions 20 which are compact in size to be readily incorporated in a small spacing in the stripped terminal crimping machine 1 in closer proximity to the bidirectional path P of the end of the cable 2. This insures a sufficient brightness and the size reduction of the terminated cable part inspection device 8 itself incorporated in the stripped terminal crimping machine 1.

Since the detecting position of the first sensor 31 is located in corresponding relation to the passing position of the end of the coating 2a at the stripped end of the cable 2, the passage of the end of the cable 2 which might suffer a failure such as disconnection of the core part 2b is satisfactorily detected. Since the detecting position R of the second sensor 32 is located in corresponding relation to the passing position of the intermediate part of the core barrel part 5a of the crimped crimp terminal 5, the detecting position R is a generally intermediate position of the photographing range as shown in FIG. 8, which can effectively solve the yawing problem of the crimp terminal 5. This provides good photographing timing by the image pickup camera 11, whether the cable 2 be transported in the first or second direction along the bidirectional path P, and stabilized image capturing.

The end of the cable 2 held in cantilevered fashion by the cable clamp portion 7a during the high-speed transport causes the distal end of the stripped part 4 to deflect slightly rearwardly in the transport direction when transported in the first direction along the bidirectional path P. The end of the cable 2 weighted by the crimp terminal 5 crimped thereto when transported in the second direction along the bidirectional path P causes the distal end of the terminal crimped part 36 to deflect by a greater amount rearwardly in the opposite transport direction. However, the provision of the respective purpose-built first and second sensors 31 and 32 can provide good photographing timing by the image pickup camera 11 and stabilized image capturing.

The light diffusing spacings 28 between the light projecting portions 23 and the transmitted light scattering plates 27 can produce uniformly scattered light for the end of the cable 2 passing along the bidirectional path P to provide illumination of high brightness. Such a structure that the diffusing spacings 28 are merely provided may reduce the costs.

Additionally, as shown in FIG. 6, the photographing path 19 of the illumination holder 25 is of rhombic configuration, and the transmitted light scattering plates 27 close the illuminating portion mounting apertures 26 on opposite sides of the photographing path 19 and are mounted and fixed in inwardly inclined relation. Such an arrangement ensures a greater light projection area of the transmitted light scattering plates 27 than the structure having the rectangular photographing path 19 and the structure having the parallel transmitted light scattering plates 27 which form 180 degrees. This provides for total improvement in illuminance at the photographing position, accordingly achieving the inspection using more correct image information and the improvement in inspection reliability.

Figure 33:
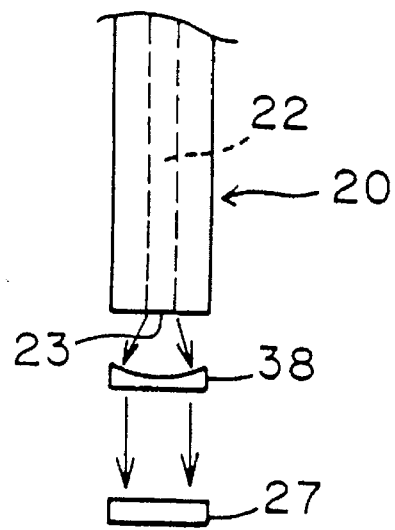
FIG. 33 illustrates another preferred embodiment according to the present invention.
Figure 34:
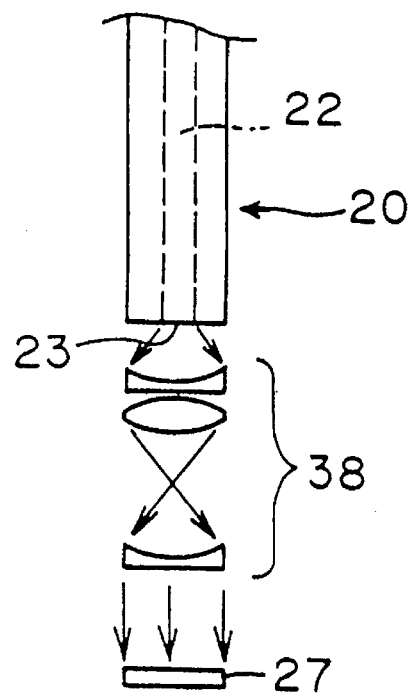
FIG. 34 illustrates another preferred embodiment according to the present invention.

Referring to FIGS. 33 and 34, one or more condenser lenses 38 may be suitably provided between the light projecting portion 23 and transmitted light scattering plate 27 to guide the light from the light projecting portion 23 in a direction at right angles to the transmitted light scattering plate 27. This provides illumination of higher illuminance by more uniformly scattered light.

The illuminating portions 20 are mounted in the illuminating portion mounting apertures 26 of the illumination holder 25 in the preferred embodiment. However, the illuminating portions 20 may be separately independently mounted to the base of the stripped terminal crimping machine 1.

The processing of the photographed reflected image is discussed below using the image of the terminal crimped part 36 transported in the second direction along the bidirectional path P.

Figure 35:
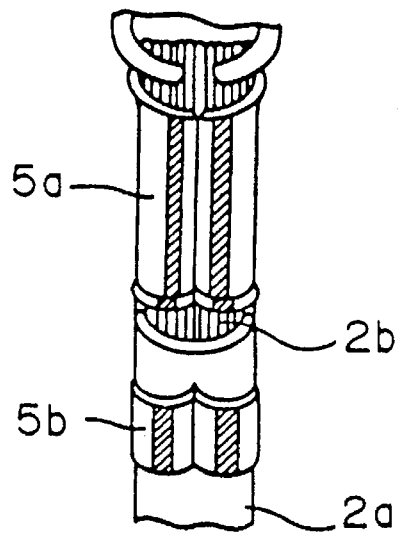
FIG. 35 illustrates an image of the cable end transported in the second direction of the first preferred embodiment.
Figure 36:
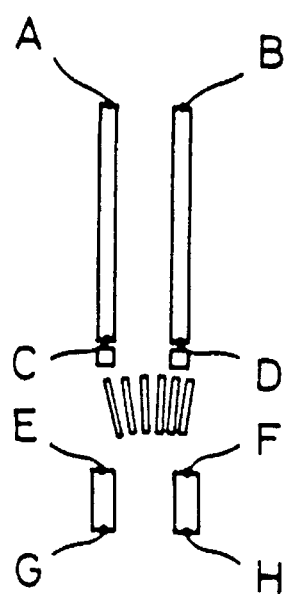
FIGS. 36 to 40, FIGS. 41A through 41C and FIGS. 42A and 42B illustrate image processing of the first preferred embodiment.

An example of the image of the terminal crimped part 36 transported in the second direction is shown in FIG. 35. The shaded portions of FIG. 35 are specular reflection parts. Specular reflection is also provided in the core part 2b between a resin barrel part 5b and the core barrel part 5a. The specular reflection parts are extracted as shown in FIG. 36.

In general, bellmouths are formed on opposite ends of the core barrel part 5a to release the stresses during the crimping of the crimp terminal 5. The bellmouths sharpen the boundary between the end of the specular reflection parts in the core barrel part 5a and the core part 2b.

Reference points for the image processing are derived by the image processing means by means of the run-length encoding technique which is detailed in the specification and accompanying drawings of Japanese Patent Application No. 3-268771 (1991) applied by the applicant of the present invention and which is based on the derivation of the configuration and the like of the crimp terminal 5 to be processed from the changes in white and black information along one scanning line.

Figure 37:
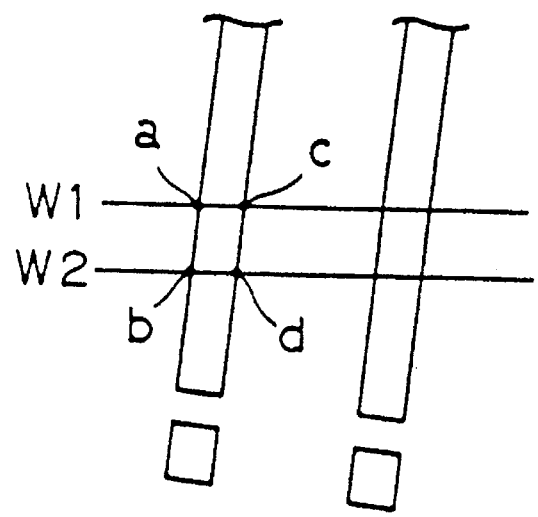
Figure 38:
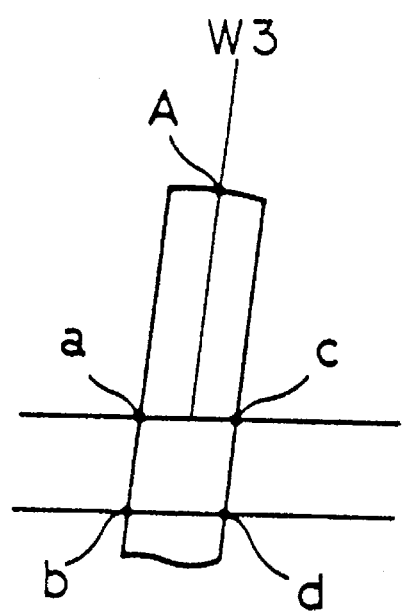

Specifically, to detect the reference points required for the image processing, two linear windows W1, W2 are established in the middle of the image of the specular reflection parts in the core barrel part 5a as shown in FIG. 37. The points a, b, c, d of intersection of the windows W1, W2 and the borders of the specular reflection parts are derived. The gradient of the specular reflection parts is determined from the gradient of the line segment ab connecting the points a and b. Then, as shown in FIG. 38, a window W3 is established which extends from the mid-point of the line segment ac or any intermediate point on the line segment ac with a gradient of the line segment ab. A point A of change in brightness is derived on the window W3 and serves as one of the reference points required for the image processing. Likewise, other reference points B, C, D, E, F, G, H shown in FIG. 36 are derived.

In practice, the barrel parts 5a and 5b are not completely formed in a cylindrical shape and provide incomplete specular surfaces to cause a geometrically unstable shape of the specular reflection parts. It is hence impracticable to determine the reference points during one process shown in FIGS. 37 and 38, and the reference points are in practice determined by repeating the process twice or three times.

Figure 39:
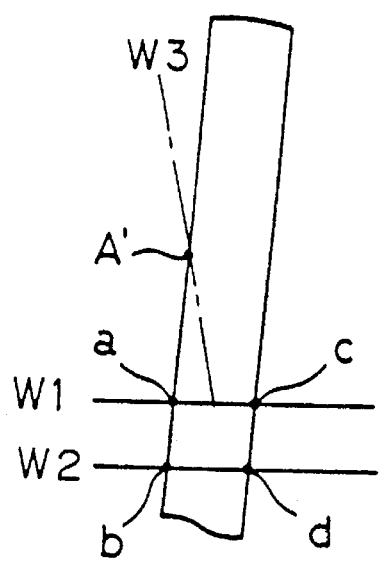
Figure 40:
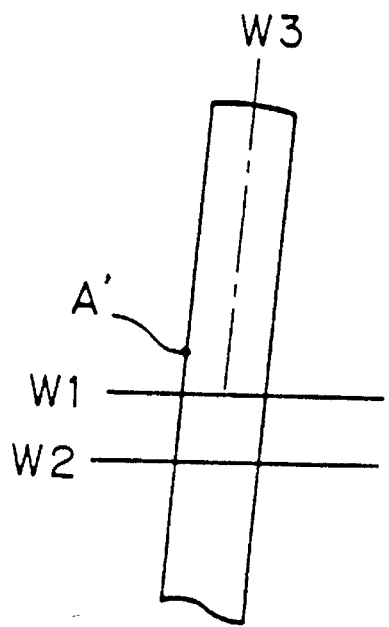

More specifically, if the window W3 is established as shown in FIG. 39 due to a gradient error based on the line segment ab of FIG. 38, a reference point A' is not located at the end of the specular reflection part. In this case, the windows W1, W2 are re-established at the positions shifted by several pixels from the derived reference point A' and the similar operation is repeated to derive the point of change in brightness on the window W3 as shown in FIG. 40.

In this manner, the repetition of the establishment of the window W3 and derivation of the brightness change point twice or three times can accurately derive the reference point A (FIG. 38).

After the reference points A to H required for the image processing are derived by the above noted procedure, the configuration, size and gradient of the crimp terminal 5 are determined on the basis of the reference points A to H, and a judgement is made whether or not the crimping conditions of the crimp terminal 5 are defective on the basis of the position of the end of the coating 2a between the resin barrel part 5band core barrel part 5a and the length of projecting core part 2b between the core barrel part 5a and a front end connecting portion.

The attitude of the crimp terminal 5 need not be completely the same because of the correct derivation of the reference points A to H. This allows an acceptable level of rough arrangement of the crimp terminal 5 to be inspected. A stable image is obtained if the crimp terminal 5 falls within the photographing range of the image pickup camera 11.

Figure 41A:
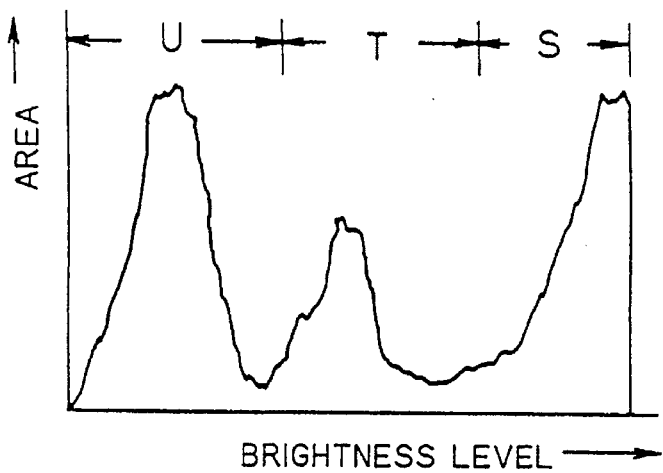

A distribution curve based on an area versus received light intensity histogram for an image of the crimp terminal 5 crimped to a blue cable 2 illuminated by the illuminating means 12 is shown, for example, in FIG. 41A wherein the abscissa is a brightness level indicated by 256 gradations and the ordinate is the area (the number of pixels). In FIG. 41A, the region of high brightness level corresponds to a specular reflection region S in the barrel parts 5a, 5b of the crimp terminal 5, the region of intermediate brightness level corresponds to a resin region T of the coating 2a of the cable 2, and the region of low brightness level corresponds to a non-specular reflection region U of the crimp terminal 5. In the distribution curve of FIG. 41A based on the area versus received light intensity histogram, there are valleys between the specular reflection region S and resin region T and between the resin region T and non-specular reflection region U.

Figure 41B:
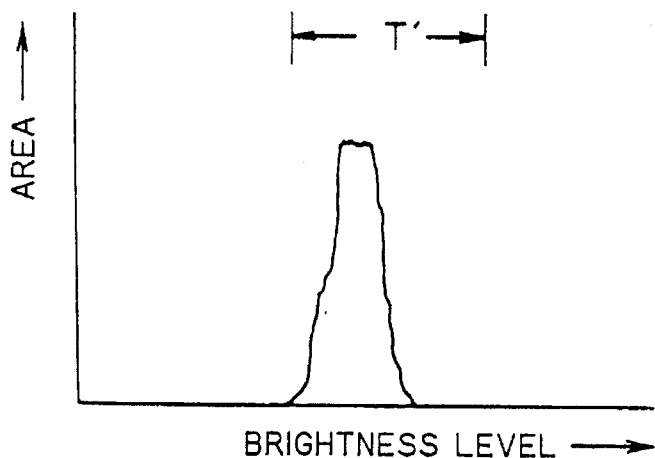

A distribution curve based on an area versus received light intensity histogram for a background image including no crimp terminal 5 is shown in FIG. 41B. There is a peak in a background region T' corresponding to the resin region T. The irregular reflector plate 34 is selected so that the background region T' is positioned intermediate the specular reflection region S and non-specular reflection region U of FIG. 41A.

Figure 41C:
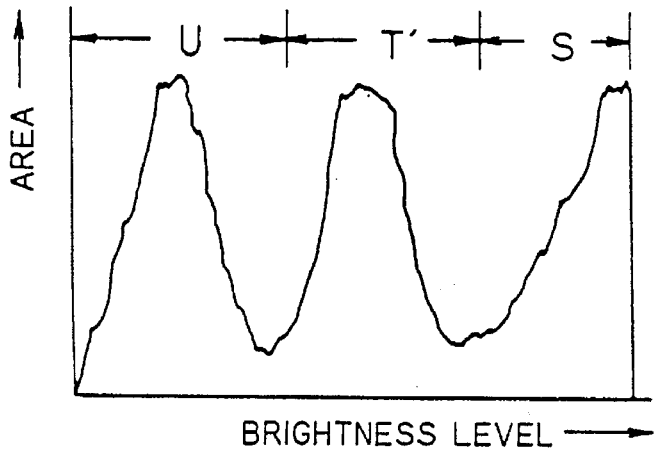

The synthesis of the distribution curves of FIGS. 41A and 41B based on the area versus received light intensity histograms is shown in FIG. 41C. In FIG. 41C, there are peaks in the specular reflection region S, background region T', and non-specular reflection region U, and there are valleys between the regions S and T' and between the regions T' and U, similarly to FIG. 41A.

For the blue cable 2, a typical distribution curve based on the area versus received light intensity histogram for the crimp terminal 5 is previously determined, and binary levels may be set between the specular reflection region S and background region T' and between the background region T' and non-specular reflection region U, that is, in the valleys of the distribution curve.

Figure 42A:
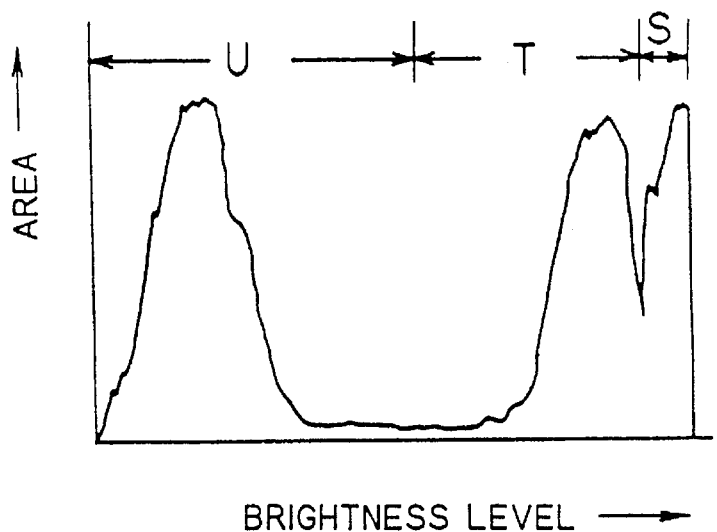
Figure 42B:
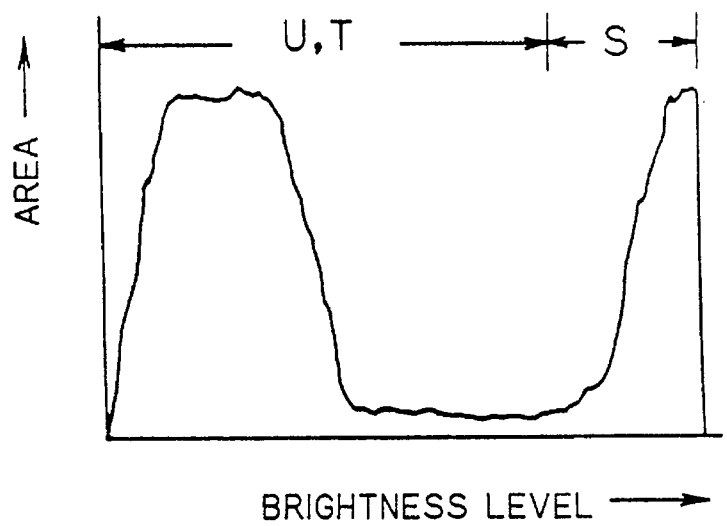

Distribution curves based on area versus received light intensity histograms when the cable 2 is white and black are shown in FIGS. 42A and 42B, respectively. With the while cable, the peak in the resin region T is shifted toward the specular reflection region S as compared with the blue cable (FIG. 41A) and there is a small valley between the regions S and T. With the black cable, the peak in the resin region T is shifted toward the non-specular reflection region U as compared with the blue cable, and the resin region T and non-specular reflection region U overlap so that the distinction therebetween is blurry. However, in the case of the white cable, the binary level may be set between the specular reflection region S and resin region T by regulating the illumination intensity using the diaphragm of the lens of the image pickup camera 11. This allows the setting of two different binary levels, that is, the above stated binary level between the specular reflection region S and resin region T and the binary level between the resin region T and non-specular reflection region U. In the case of the black cable, one binary level is reliably set in a wide, distinct valley between the resin and non-specular reflection regions T, U and the specular reflection region S.

Thus two binary levels may be set for the while cable 2, similar to the blue cable, by previously determining the typical distribution curve based on the area versus received light intensity histogram for the crimp terminal 5. For the black cable, although one binary level may be definitely set on the basis of the distribution curve, another binary level may be readily set in a low brightness level region, if required, on the basis of various distribution curves based on area versus received light intensity histograms.

The setting of two different binary levels on the basis of the distribution curve based on the area versus received light intensity histogram for the image of the crimp terminal 5 toward which illumination is directed by the illuminating portions 20 and irregular reflector plate 34 in opposite directions insures the detection of the core part 2b extending off, particularly the core part 2b extending off sidewise.

Figure 43A:
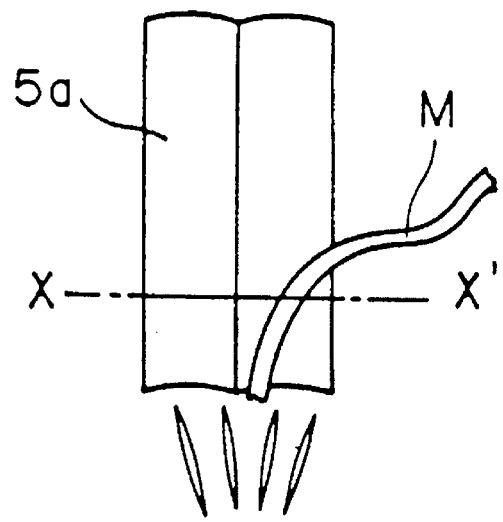
FIGS. 43A, 43B, 44 and 45 illustrate the operation of the first preferred embodiment.
Figure 43B:
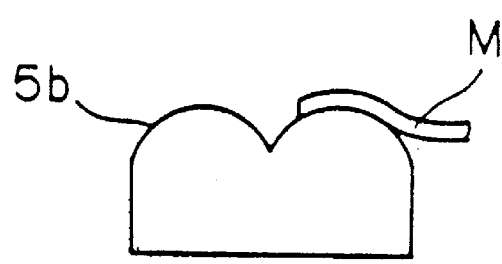
Figure 44:
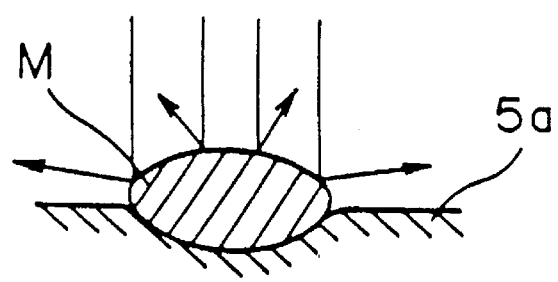

For example, when the crimp terminal 5 is crimped to the cable, with one core M extending off over the core barrel part 5a as shown in FIGS. 43A and 43B, then the extending-off core M reflects light from the illuminating portions 20 as shown by the arrows of FIG. 44 which is an enlarged sectional view taken along the line X–X' of FIG. 43A. Since this reflection causes partially irregular reflection in the specular reflection parts in the core barrel part 5a, the core M extending off over the core barrel part 5a is definitely detected by the binary processing using one binary level. Therefore, the core M extending off over the core barrel part 5a is detected by the presence of partially irregular reflection in the specular reflection parts in the core barrel part 5a. FIG. 43B is a front view of FIG. 43A which is a plan view.

Figure 45:
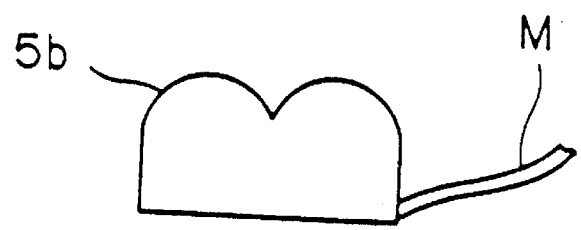
Figure 46:
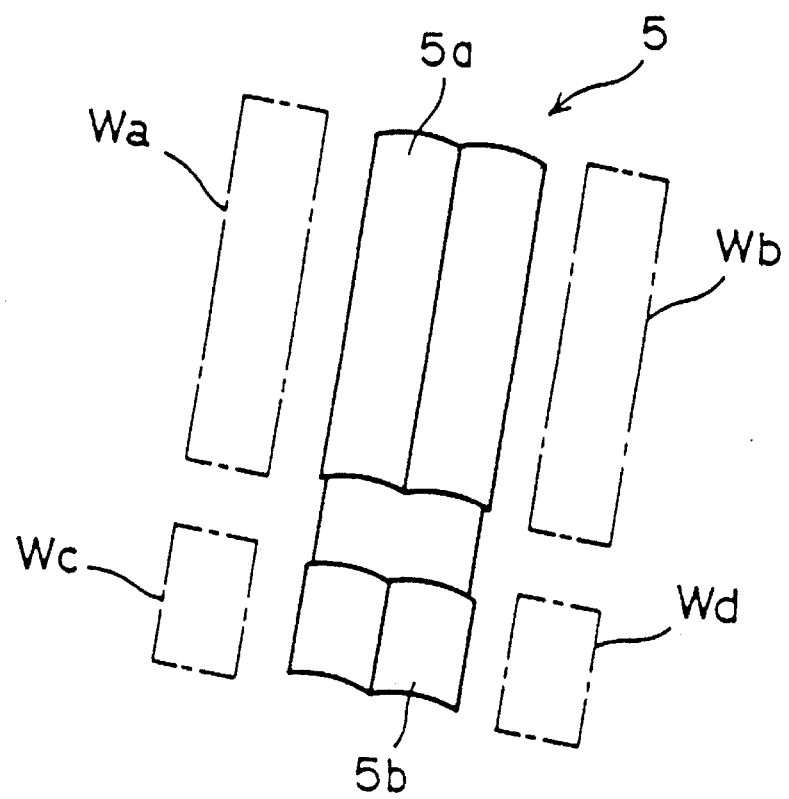
FIGS. 46 and 47 illustrate image processing of the first preferred embodiment.
Figure 47:
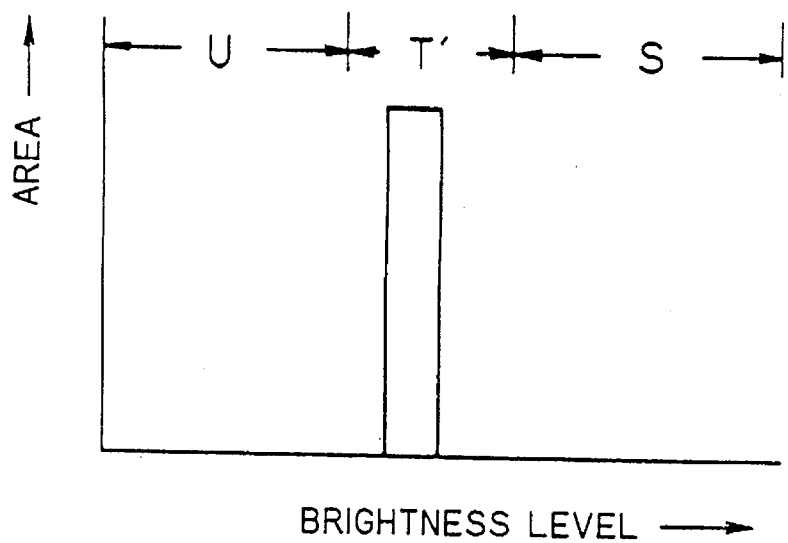

When the core M is extending off sidewise from the crimp terminal 5 as shown in FIG. 45, the illuminating portions 20 and irregular reflector plate 34 direct illumination in the opposite directions toward the crimp terminal 5 to obtain an image of the crimp terminal 5. On the image of the crimp terminal 5 as shown in FIG. 46, rectangular windows Wa, Wb are established on opposite sides of the core barrel part 5a and rectangular windows Wc, Wd are similarly established on opposite sides of the resin barrel part 5b. The distribution curve based on the area versus received light intensity histogram for the windows Wa to Wd is shown in FIG. 47 if the core M does not extend off. In the distribution curve of FIG. 47, there is a peak only in the background region T', and no peaks appear in the regions S and U.

The core M extending off sidewise from the crimp terminal 5 generates a peak in the region S or U in addition to the peak in the background region T' in the distribution curve for any of the windows Wa to Wd. Thus the binary processing is performed on the brightness of each pixel in each of the windows Wa to Wd on the basis of the binary levels set between the regions S and T' and between regions T' and U, and the presence of a pixel having a brightness higher than the higher binary level between the regions S and T' and a pixel having a brightness lower than the lower binary level between the regions T' and U is detected, thereby detecting the core M extending off sidewise from the crimp terminal 5 in any direction.

Figure 48A:
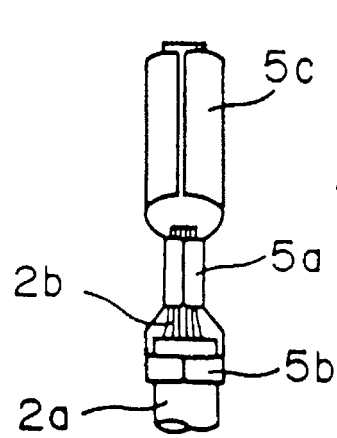
FIGS. 48A, 48B, 49A, 49B, 50A and 50B illustrate the operation of the first preferred embodiment.
Figure 48B:
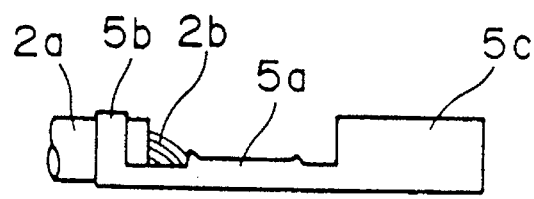

As a result of the image processing, it is judged that the crimping conditions of the crimp terminal 5 are good, when the resin barrel part 5b grasps the coating 2a, with the coating 2a of the cable 2 extending by a suitable length between the resin barrel part 5b and core barrel part 5a of the crimp terminal 5, and the core barrel part 5a grasps the core part 2b, with the core part 2b slightly exposed between the core barrel part 5a and a front end connecting part 5c, as shown in FIGS. 48A and 48B.

Figure 49A:
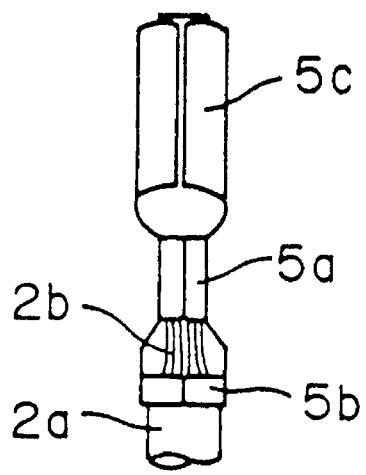
Figure 49B:
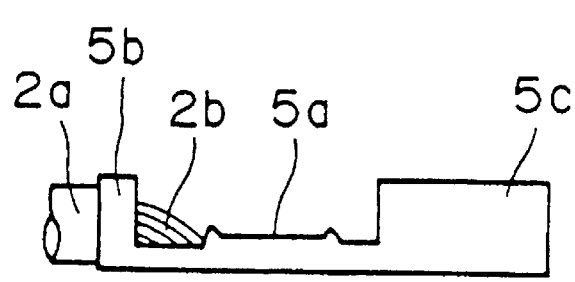

As a result of the image processing, a so-called resin part crimping failure is judged, when the coating 2a of the cable 2 does not appear between the resin barrel part 5b and core barrel part 5a of the crimp terminal 5 and the resin barrel part 5b grasps the end of the coating 2a as shown in FIGS. 49A and 49B.

Figure 50A:
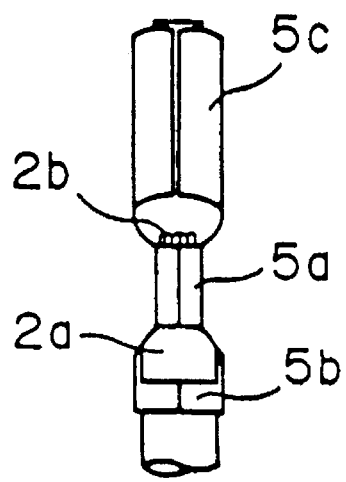
Figure 50B:
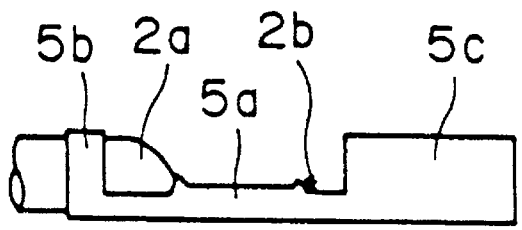

As a result of the image processing, a so-called resin engagement failure is judged, when the core barrel part 5a of the crimp terminal 5 grasps the end of the coating 2a and the core part 2b does not appear between the resin barrel part 5b and core barrel part 5a as shown in FIGS. 50A and 50B.

Other failures may be detected as a result of the image processing, for example, the above stated core extending-off failure, a so-called pressing failure in which the resin barrel part 5b is open, and a short core failure in which no end of the core part 2b extends from the core barrel part 5a. These failures detected are subjected to suitable corrective actions.

Although the image processing of the terminal crimped part 36 fed in the second direction along the bidirectional path P has been described above, the image processing of the stripped part 4 fed in the first direction therealong may be similarly performed.

In the processing using the photographed reflected image, other image processing methods may be used for quality judgement.

While the invention has been shown and described in detail, the foregoing description is in all aspects illustrative and not restrictive. It is therefore understood that numerous modifications and variations can be devised without departing from the scope of the invention.

We claim:

1. A method for illumination in a terminated cable part inspection device for a stripped terminal crimping machine, said stripped terminal crimping machine comprising a stripping portion for stripping a coating at an end of a cable, a terminal crimping portion for crimping a crimp terminal to the stripped end of the cable, and a transport mechanism for transporting the stripped cable end in a first direction along a bidirectional path from an initial position of the bidirectional path to the terminal crimping portion and then transporting the stripped cable end in a second direction along the bidirectional path from the terminal crimping portion to the initial position after crimping of the crimp terminal, said terminated cable part inspection device for photographing the cable end transported along the bidirectional path to inspect a stripped part and a terminal crimped part of the cable by image processing, said terminated cable part inspection device including an image pickup camera for photographing the cable end, and illuminating means for illuminating the cable end to be photographed by said image pickup camera, said illuminating means including a pair of illuminating portions on opposite sides of a photographing path of said image pickup camera for directing illumination in substantially the same direction as a photographing direction of said image pickup camera toward the cable end passing therethrough along the bidirectional path, said pair of illuminating portions being elongated in substantially the same direction as a longitudinal direction of the cable, said method comprising directing illumination by said pair of illuminating portions in inwardly angled directions respectively from the opposite sides of the photographing path of said image pickup camera toward the cable end passing therethrough along the bidirectional path.

2. An illuminating device for use in a terminated cable part inspection device for a stripped terminal crimping machine, said stripped terminal crimping machine comprising a stripping portion for stripping a coating at an end of a cable, a terminal crimping portion for crimping a crimp terminal to the stripped end of the cable, and a transport mechanism for transporting the stripped cable end in a first direction along a bidirectional path from an initial position of the bidirectional path to the terminal crimping portion and then transporting the stripped cable end in a second direction along the bidirectional path from the terminal crimping portion to the initial position after crimping of the crimp terminal, said terminated cable part inspection device for photographing the cable end transported along the bidirectional path to inspect a stripped part and a terminal crimped part of the cable by image processing, said terminated cable part inspection device including an image pickup camera for photographing the cable end, and illuminating means for illuminating the cable end to be photographed by said image pickup camera, said illuminating means including a pair of illuminating portions on opposite sides of a photographing path of said image pickup camera for directing illumination in substantially the same direction as a photographing direction of said image pickup camera toward the cable end passing therethrough along the bidirectional path, said pair of illuminating portions being elongated in substantially the same direction as a longitudinal direction of the cable, wherein said pair of illuminating portions are arranged in inwardly inclined relation.

3. The illuminating device of claim 2, wherein said image pickup camera has a high shutter speed, wherein said terminated cable part inspection device further includes a first sensor for detecting a timing of photographing the cable end transported in the first direction along the bidirectional path by said image pickup camera, and a second sensor for detecting a timing of photographing the cable end transported in the second direction along the bidirectional path by said image pickup camera, said first and second sensors being located in positions deviated from an optical axis of said image pickup camera, and wherein the detection position of said first sensor is positioned in corresponding relation to a passing position of an end of the coating at the stripped cable end, and the detection position of said second sensor is positioned in corresponding relation to a passing position of an intermediate part of a core crimping part of the crimped crimp terminal.

4. The illuminating device of claim 2, wherein said image pickup camera has a high shutter speed, and wherein said terminated cable part inspection device further includes an optical fiber for guiding light emitted from a light source to light projecting portions of said illuminating portions, a first sensor for detecting a timing of photographing the cable end transported in the first direction along the bidirectional path by said image pickup camera, and a second sensor for detecting a timing of photographing the cable end transported in the second direction along the bidirectional path by said image pickup camera, said first and second sensors being located in positions deviated from an optical axis of said image pickup camera.

5. The illuminating device of claim 4, wherein the detection position of said first sensor is positioned in corresponding relation to a passing position of an end of the coating at the stripped cable end, and the detection position of said second sensor is positioned in corresponding relation to a passing position of an intermediate part of a core crimping part of the crimped crimp terminal.

6. The illuminating device of claim 4, wherein each of said pair of illuminating portions includes a transmitted light scattering plate between said bidirectional path and each of said light projecting portions projecting the light guided by said optical fiber, so as to form a spacing between each of said light projecting portions and said transmitted light scattering plate for diffusing light.

7. The illuminating device of claim 6, wherein said illuminating means further includes an illumination holder of a hollow, cuboid-shaped configuration, wherein said photographing path is of a rhombic configuration along the optical path of said image pickup camera and is located in the center of said illumination holder, wherein illuminating portion mounting apertures for mounting said illuminating portions therein, respectively, are provided on opposite sides of said photographing path of said illumination holder, and wherein said transmitted light scattering plates close the ends of said illuminating portion mounting apertures and are mounted in inwardly inclined relation.

8. The illuminating device of claim 4, wherein each of said pair of illuminating portions includes a transmitted light scattering plate between said bidirectional path and each of said light projecting portions projecting the light guided by said optical fiber, and a condenser lens between each of said light projecting portions and said transmitted light scattering plate for guiding the light projected from each of said light projecting portions in a direction at right angles to said transmitted light scattering plate.

9. The illuminating device of claim 4, further comprising:

an irregular reflector plate opposed to said illuminating portions, with the bidirectional path therebetween.

* * * * *